(12) United States Patent
Maryanoff et al.

(10) Patent No.: US 6,218,384 B1
(45) Date of Patent: Apr. 17, 2001

(54) 3-OXO-PYRIDO(1,2-A)BENZIMIDAZOLE-4-CARBOXYL AND 4-OXO-AZEPINO(1,2-A)BENZIMIDAZOLE-5-CARBOXYL DERIVATIVES USEFUL IN TREATING CENTRAL NERVOUS SYSTEM DISORDERS

(75) Inventors: Bruce E. Maryanoff, New Hope; David F. McComsey, Warminster; Winston Ho, North Wales, all of PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 08/896,301

(22) Filed: Jun. 30, 1997

Related U.S. Application Data

(60) Division of application No. 08/387,720, filed on Feb. 16, 1995, now Pat. No. 5,639,760, which is a continuation-in-part of application No. 07/932,176, filed on Aug. 19, 1992, now abandoned.

(51) Int. Cl.⁷ .................... C07D 487/04; A61K 31/4184; A61P 25/00
(52) U.S. Cl. ...................................... 514/214.02; 540/579
(58) Field of Search ............................. 540/579; 514/214, 514/214.02

(56) References Cited

PUBLICATIONS

Ohta et al. (Chem. Pharm. Bull. 39(11) 2787–2792), Nov. 1991.*

* cited by examiner

*Primary Examiner*—Bruck Kifle

(57) ABSTRACT

A compound of the general formula I;

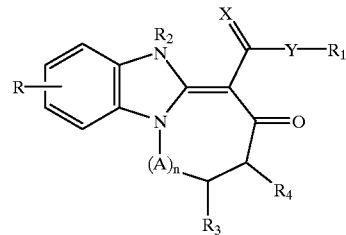

is disclosed as useful in treating disorders of the central nervous system. Pharmaceutical compositions and methods of treatment are also disclosed.

19 Claims, No Drawings

3-OXO-PYRIDO(1,2-A)BENZIMIDAZOLE-4-CARBOXYL AND 4-OXO-AZEPINO(1,2-A) BENZIMIDAZOLE-5-CARBOXYL DERIVATIVES USEFUL IN TREATING CENTRAL NERVOUS SYSTEM DISORDERS

This application is a divisional of application Ser. No. 08/387,720, filed Feb. 16, 1995, now U.S. Pat. No. 5,639,760 which is a continuation-in-part of application Ser. No. 07/932,176, filed Aug. 19, 1992 now abandoned.

BACKGROUND OF THE INVENTION

The gamma-aminobutyric acid-A receptor (GABA-A receptor) is the most abundant inhibitory receptor in mammalian brain. It is comprised of a heteropolymeric structure that forms a chloride ion channel, and bears multiple recognition sites for the binding of modulatory molecules. The binding of GABA to its specific recognition site on the GABA-A receptor opens the ion channel and allows chloride ions to flow into the nerve cell. This action hyperpolarizes the cell membrane of that neuron and thereby makes the cell less reactive to excitatory stimuli. The chloride ion current may also be regulated by various drugs that serve as positive or negative modulators of the GABA-A receptor (Puia, G. et al. *Molecular Pharm.* 1991, 39, 691). The so-called benzodiazepine (BZD) receptor is a site for such allosteric modulators on the GABA-A receptor. This site mediates two opposing effects, one that amplifies the action of GABA ("positive" efficacy) and the other that reduces the action of GABA ("negative" efficacy). Agents facilitating GABA-receptor/chloride ion-channel functions via the BZD site are referred to as agonists, while agents reducing such function are referred to as inverse agonists. Antagonists at this site block the effects of agonists or inverse agonists by competitively inhibiting their binding. It is thus possible to have a series of compounds in which members equally bind to the BZD site but have equal and opposite regulatory effects on the GABA-A receptor/chloride ion channel. Also, within the series a continuum of activity is possible (Takada, S. et al. *J. Med. Chem.* 1988, 31, 1738). Thus, BZD receptor ligands can induce a wide spectrum of pharmacological effects ranging from muscle relaxant, hypnotic, sedative, anxiolytic, and anticonvulsant activities, produced by full or partial agonists ("positive"), to the proconvulsant, anti-inebriant, and anxiogenic activities, produced by inverse agonists ("negative"). (A further understanding of this area can be gleaned from: Mohler, H. *Arzneim.-Forsch./Drug Res.* 1992, 42 (2a), 211; Haefely, W. et al., *Advances in Drug Research,* Academic Press, vol. 14, 1985, pp. 165–322; Skolnick, P. et al., GABA and Benzodiazepine Receptors, Squires, R., Ed., 1987, pp. 99–102 and references cited therein.)

The benzodiazepines are a class of compounds which bind to the BZD receptor with high affinity. Most of the drugs in use are agonist-type ligands for the receptor. Such compounds are generally useful for their anticonvulsant, anxiolytic, sedative, and muscle relaxant effects. Antagonists of the BZD binding site are useful for the treatment of benzodiazepine drug overdose and inverse agonists are useful in managing alcoholism.

The present invention is concerned with novel compositions of matter based on 3-oxo-pyrido(1,2-a)benzimidazole-4-carboxyl and 4-oxo-azepino(1,2-a)benzimidazole-5-carboxyl derivatives. Compounds having some structural similarity to those of the present invention are described in Rida, S. M. et al. *J. Het. Chem.* 1988, 25, 1087; Soliman, F. S. G. et al. *Arch. Pharm.* 1984, 317, 951; Volovenko, Y. M. et al. U.S.S.R. Patent SU 1027166 (*Chem Abs.* 99(25) 212524t); Ohta, S. et al. *Heterocycles* 1991, 32, 1923; Ohta, S. et al. *Chem. Pharm. Bull.* 1991, 39, 2787.

SUMMARY OF THE INVENTION

The present invention is directed to compounds of the following formula I:

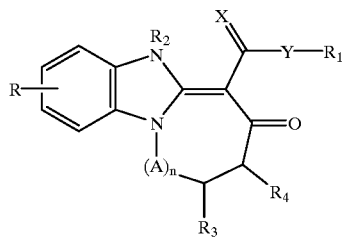

wherein R, $R_1$, $R_2$, $R_3$, $R_4$, A, n, X, and Y are as defined hereinafter. The compounds of formula I are useful in treating central nervous system disorders. The compounds are ligands for the BZD binding site on GABA-A receptors, and are thus useful as muscle relaxants, hypnotics/sedatives including sleep-aids, anxiolytics, anticonvulsants/antiepileptics, anti-inebriants, and antidotes for drug overdose (particularly benzodiazepine overdose).

The present invention also comprises pharmaceutical compositions containing one or more of the compounds of formula I and methods for the treatment of disorders to the central nervous system including convulsions such as epileptic seizures, anxiety, muscular spasms, sleep disorders, and benzodiazepine overdoses employing a compound of formula I.

DETAILED DESCRIPTION OF THE INVENTION

More specifically, the invention is directed to compounds of the following formula I:

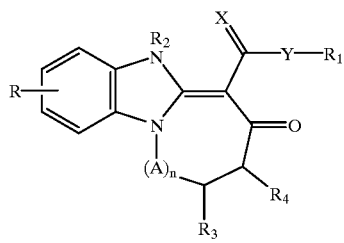

wherein $R_1$ is selected from any of alkyl ($C_1$–$C_{12}$), cycloalkyl ($C_3$–$C_{10}$), phenyl; substituted phenyl where there are one or more substituents which are independently selected from any of halogen, alkyl ($C_1$–$C_5$), perfluoro(lower)alkyl, nitro, lower alkoxy, hydroxy, amino, lower alkylamino, di(loweralkyl)amino, di(loweralkyl)aminoalkyl, carboxy, lower alkoxycarbonyl, aminocarbonyl, lower alkylthio, cyano, and aminosulfonyl; aralkyl and substituted aralkyl where the aryl substituents are as described above with respect to substituted phenyl; a heterocycle where the heterocycle is selected from any of pyridine, thiazole, thiophene, furan, indole, benzothiophene, pyridazine, pyrimidine, indole, indoline, quinoline, indazole, imidazole, benzofuran, triazine, pyrazine, isoquinoline, isoxazole, thiadiazole, benzothiazole, triazole or benzotriazole; a substituted heterocycle where there are one or more substituents which are independently selected from any of halogen, perfluoro(lower)alkyl, nitro, lower alkylthio, lower alkoxy, lower alkyl, di(lower alkyl)amino, carboxy, lower alkoxycarbonyl, piperidin-3-yl, piperidin-4-yl, morpholin-4-yl, heterocyclic -CH$_2$—, heterocyclic-CH$_2$CH$_2$—, or substituted heterocyclic-CH$_2$— and heterocyclic-CH$_2$CH$_2$— (where the heterocycle is as previously defined and where the substituent groups are as previously defined for the heterocycle group). More preferably, R$_1$ is selected from any of alkyl (C$_1$–C$_{12}$), cycloalkyl (C$_3$–C$_{10}$), phenyl, substituted phenyl (where the substituents are independently selected from the group consisting of halogen, perfluoro(lower) alkyl, nitro, lower alkoxy, lower alkyl, hydroxy, amino, di(lower alkyl) amino, lower alkoxycarbonyl, lower alkylthio, cyano and aminosulfonyl), aralkyl, a heterocycle selected from any of pyridine, pyridinylmethyl, thiazole, pyrimidine, indoline, quinoline, indazole, benzofuran, triazine, pyrazine, isoquinoline, isoxazole, thiazole, thiadiazole, benzothiazole, triazole, or benzotriazole, or a substituted heterocycle from the preferred group of heterocycles which are pyridine, isoxazole, thiadiazole, and quinoline (where there is one or more substituents which are independently selected from any of halogen, perfluoro (lower) alkyl, nitro, lower alkylthio, lower alkoxy, lower alkyl, di(lower alkyl)amino, carboxy, lower alkoxycarbonyl).

R$_2$ is selected from any of hydrogen, alkyl (C$_1$–C$_{12}$), cycloalkyl (C$_3$–C$_{10}$), aralkyl and substituted aralkyl, where the aryl substituents are as previously defined in connection with the definition of R$_1$. R$_2$ is more preferably any of H, lower alkyl or aralkyl.

R is selected from one or more of hydrogen, alkyl (C$_1$–C$_8$), branched alkyl (C$_3$–C$_8$), halogens, perfluoro(lower alkyl), hydroxy, lower alkoxy, di(lower alkyl) amino, lower alkoxycarbonyl or lower alkylthio. There may be up to 4 independent R substituents on the phenyl. More preferably, R is selected from any of lower alkoxy, H, halogen or alkyl (C$_1$–C$_8$). Preferably, there is only one R substituent other than H.

n is selected from zero or 1.

A is selected from methylene or substituted methine where the substituents are selected from the group consisting of alkyl (C$_1$–C$_2$). More preferably, A is methylene.

R$_3$ and R$_4$ are independently selected from hydrogen, alkyl (C$_1$–C$_3$) or may be taken together to form a double bond within the ring. R$_3$ and R$_4$ are more preferably selected from any of hydrogen or are taken together to form a double bond.

X is selected from oxygen or sulfur.

Y is selected from NH, oxygen or sulfur, provided that when R$_1$ is an alkyl or a heterocycle or substituted heterocycle, Y may not be sulfur or oxygen; and Y and R$_1$ may also be taken together to form an NH$_2$ group.

As used herein unless otherwise noted alkyl and alkoxy whether used alone or as part of a substituent group, include straight and branched chains. For example, alkyl radicals include methyl, ethyl, propyl, isopropyl, butyl, isobutyl, sec-butyl, t-butyl, pentyl, 2-methyl-3-butyl, 1-methylbutyl, 2-methylbutyl, neopentyl, hexyl, 1-methylpentyl, 3-methylpentyl. Alkoxy radicals are oxygen ethers formed from the previously described straight or branched chain alkyl groups. Unless otherwise noted, "lower" when used with alkyl and alkoxy means a carbon chain composition of 1–5 carbon atoms. Of course, if the alkyl or alkoxy substituent is branched there must be at least 3 carbons.

The term "aryl" as used herein alone or in combination with other terms indicates aromatic hydrocarbon groups such as phenyl or naphthyl. The term "aralkyl" means a radical containing a lower alkyl group substituted with an aryl radical. With reference to substituents, the term independently means that when more than one of such substituent is possible, such substituents may be the same or different from each other.

The definition of formula I as shown in the specification and as used in the claims includes possible isomers, such as tautomers and rotamers. The formulas Ia and Ib (below) illustrate this point.

For formula I, when R$_2$=H:

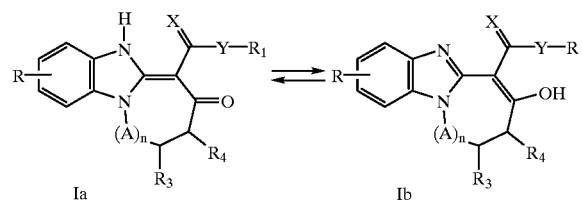

Ia                    Ib

The definition of formula I, however, does not include any of the following compounds, 1,2-dihydro-3-hydroxy-N-(2-trifluoromethylphenyl)-pyrido(1,2-a)benzimidazole-4-carboxamide; i.e., where X is O, Y is NH, R is H, n=0, R$_1$ is 2-trifluoromethylphenyl, R$_2$ is H, R$_3$ and R$_4$ are H; 8-chloro-1,2-dihydro-3-hydroxy-N-(4-pyridyl)-pyrido(1,2-a)benzimidazole-4-carboxamide; i.e., where X is O, Y is NH, R is 8-Cl, n=0, R$_1$ is pyridin-4-yl, R$_2$ is H, and R$_3$ and R$_4$ are H; N-(4-(dimethylamino)phenyl)-8-chloro-1,2-dihydro-3-hydroxypyrido(1,2-a)benzimidazole-4-carboxamide; i.e., where X is O, Y is NH, R is 8-Cl, n=0, R$_1$ is 4-dimethylaminophenyl, R$_2$ is H, and R$_3$ and R$_4$ are H; and 1,2-dihydro-N-(2-dimethylamino-4-fluorophenyl)-3-hydroxypyrido(1,2-a)benzimidazole-4-carboxamide; i.e., where X is O, Y is NH, R is H, n=0, R$_1$ is 2-dimethylamino-4-fluorophenyl, R$_2$ is H and R$_3$ and R$_4$ is H. The claims should be read not to include these compounds. To date, none of these compounds has exhibited biological activity in the screens in which they have been tested.

Examples of particularly preferred compounds of formula I include:

1,2-Dihydro-3-hydroxy-N-phenylpyrido(1,2-a) benzimidazole-4-carboxamide, i.e., where R, R$_2$, R$_3$, and R$_4$ are hydrogen, R$_1$ is phenyl, Y is NH, X is oxygen, and n=0 in formula 1.

1,2-Dihydro-3-hydroxy-N-(4-pyridyl)pyrido(1,2-a) benzimidazole-4-carboxamide, i.e., where R, R$_2$, R$_3$, and R$_4$ are hydrogen, R$_1$ is 4-pyridyl, Y is NH, X is oxygen, and n=0 in formula I.

1,2-Dihydro-N-(4-dimethylaminophenyl)-3-hydroxypyrido (1,2-a) benzimidazole-4-carboxamide, i.e., where R, R$_2$, R$_3$, and R$_4$ are hydrogen, R$_1$ is 4-dimethylaminophenyl, Y is NH, X is oxygen, and n=0 in formula I.

1,2-Dihydro-N-(2-fluorophenyl)-3-hydroxypyrido(1,2-a) benzimidazole-4-carboxamide, i.e., where R, R$_2$, R$_3$, and R$_4$ are hydrogen, R$_1$ is 2-fluorophenyl, Y is NH, X is oxygen, and n=0 in formula I.

1,2-Dihydro-3-hydroxy-N-(2,4,6-trifluorophenyl)pyrido(1, 2-a) benzimidazole-4-carboxamide, i.e., where R, R$_2$, R$_3$, and R$_4$ are hydrogen, R$_1$ is 2,4,6-trifluorophenyl, Y is NH, X is oxygen, and n=0 in formula I.

5-Methyl-3-oxo-N-phenyl-1,2,3,5-tetrahydropyrido(1,2-a) benzimidazole-4-carboxamide, i.e., where R, R$_3$, and R$_4$ are hydrogen, $R_2$ is methyl, $R_1$ is phenyl, Y is NH, X is oxygen, and n=0 in formula I.

5-Ethyl-3-oxo-N-phenyl-1,2,3,5-tetrahydropyrido(1,2-a) benzimidazole-4-carboxamide, i.e., where R, $R_3$, and $R_4$ are hydrogen, $R_2$ is ethyl, $R_1$ is phenyl, Y is NH, X is oxygen, and n=0 in formula I.

N-(2-Fluorophenyl)-5-methyl-3-oxo-1,2,3,5-tetrahydropyrido(1,2-a) benzimidazole-4-carboxamide, i.e., where R, $R_3$, and $R_4$ are hydrogen, $R_2$ is methyl, $R_1$ is 2-fluorophenyl, Y is NH, X is oxygen, and n=0 in formula I.

5-Ethyl-N-(2-fluorophenyl)-3-oxo-1,2,3,5-tetrahydropyrido (1,2-a) benzimidazole-4-carboxamide, i.e. where R, $R_3$, and $R_4$ are hydrogen, $R_2$ is ethyl, $R_1$ is 2-fluorophenyl, Y is NH, X is oxygen, and n=0 in formula I.

1,2-Dihydro-3-hydroxy-N-(2-phenylethyl)pyrido(1,2-a) benzimidazole-4-carboxamide, i.e., where R, $R_2$, $R_3$, and $R_4$ are hydrogen, $R_1$ is 2-(phenyl)ethyl, Y is NH, X is oxygen, and n=0 in formula I.

1,2-Dihydro-3-hydroxy-N-(2-thiazolyl)pyrido(1,2-a) benzimidazole-4-carboxamide, i.e., where R, $R_2$, $R_3$, and $R_4$ are hydrogen, $R_1$ is 2-thiazolyl, Y is NH, X is oxygen, and n=0 in formula I.

1,2-Dihydro-3-hydroxy-N-(4-methoxyphenyl)pyrido(1,2-a) benzimidazole-4-carboxamide, i.e., where R, $R_2$, $R_3$, and $R_4$ are hydrogen, $R_1$ is 4-methoxyphenyl, Y is NH, X is oxygen, and n=0 in formula I.

N-(4-Chlorophenyl)-1,2-dihydro-3-hydroxy-pyrido(1,2-a) benzimidazole-4-carboxamide, i.e., where R, $R_2$, $R_3$, and $R_4$ are hydrogen, $R_1$ is 4-chlorophenyl, Y is NH, X is oxygen, and n=0 in formula I.

N-(3-Chlorophenyl)-1,2-dihydro-3-hydroxy-pyrido(1,2-a) benzimidazole-4-carboxamide, i.e., where R, $R_2$, $R_3$, and $R_4$ are hydrogen, $R_1$ is 3-chlorophenyl, Y is NH, X is oxygen, and n=0 in formula I.

N-Cyclohexyl-1,2-dihydro-3-hydroxy-pyrido(1,2-a) benzimidazole-4-carboxamide, i.e., where R, $R_2$, $R_3$, and $R_4$ are hydrogen, $R_1$ is cyclohexyl, Y is NH, X is oxygen, and n=0 in formula I.

1,2-Dihydro-N-(3,4-dimethoxyphenyl)-3-hydroxy-pyrido (1,2-a)benzimidazole-4-carboxamide, i.e., where R, $R_2$, $R_3$, and $R_4$ are hydrogen, $R_1$ is 3,4-dimethoxyphenyl, Y is NH, X is oxygen, and n=0 in formula I.

1,2-Dihydro-3-hydroxy-N-(4-hydroxyphenyl)pyrido(1,2-a) benzimidazole-4-carboxamide, i.e., where R, $R_2$, $R_3$, and $R_4$ are hydrogen, $R_1$ is 4-hydroxyphenyl, Y is NH, X is oxygen, and n=0 in formula I.

1,2-Dihydro-3-hydroxy-N-(3-pyridyl)pyrido(1,2-a) benzimidazole-4-carboxamide, i.e., where R, $R_2$, $R_3$, and $R_4$ are hydrogen, $R_1$ is 3-pyridyl, Y is NH, X is oxygen, and n=0 in formula I.

1,2-Dihydro-3-hydroxy-7-methoxy-N-(phenyl)pyrido(1,2-a)benzimidazole-4-carboxamide, i.e., where R is 7-methoxy, $R_2$, $R_3$ and $R_4$ are hydrogen, $R_1$ is phenyl, Y is NH, X is oxygen, and n=0 in formula I.

1,2-Dihydro-3-hydroxy-7-methoxy-N-(4-methoxyphenyl) pyrido(1,2-a)benzimidazole-4-carboxamide, i.e., where R is 7-methoxy, $R_2$, $R_3$ and $R_4$ are hydrogen, $R_1$ is 4-methoxyphenyl, Y is NH, X is oxygen, and n=0 in formula I.

1,2-Dihydro-3-hydroxy-N-(phenyl)-7-trifluoromethyl-pyrido(1,2-a)benzimidazole-4-carboxamide, i.e., where R is 7-trifluoromethyl, $R_2$, $R_3$ and $R_4$ are hydrogen, $R_1$ is phenyl, Y is NH, X is oxygen, and n=0 in formula I.

1,2-Dihydro-3-hydroxy-N-(3-methoxyphenyl)pyrido(1,2-a) benzimidazole-4-carboxamide, i.e., where R, $R_2$, $R_3$, and $R_4$ are hydrogen, $R_1$ is 3-methoxyphenyl, Y is NH, X is oxygen, and n=0 in formula I.

1,2-Dihydro-3-hydroxy-N-(2-pyridyl)pyrido(1,2-a) benzimidazole-4-carboxamide, i.e., where R, $R_2$, $R_3$, and $R_4$ are hydrogen, $R_1$ is 2-pyridyl, Y is NH, X is oxygen, and n=0 in formula I.

N-(2-Chlorophenyl)-1,2-dihydro-3-hydroxy-pyrido(1,2-a) benzimidazole-4-carboxamide, i.e., where R, $R_2$, $R_3$, and $R_4$ are hydrogen, $R_1$ is 2-chlorophenyl, Y is NH, X is oxygen, and n=0 in formula I.

1,2-Dihydro-3-hydroxy-N-(2-methylphenyl)pyrido(1,2-a) benzimidazole-4-carboxamide, i.e., where R, $R_2$, $R_3$, and $R_4$ are hydrogen, $R_1$ is 2-methylphenyl, Y is NH, X is oxygen, and n=0 in formula I.

1,2-Dihydro-3-hydroxy-N-(benzyl)pyrido(1,2-a) benzimidazole-4-carboxamide, i.e., where R, $R_2$, $R_3$, and $R_4$ are hydrogen, $R_1$ is benzyl, Y is NH, X is oxygen, and n=0 in formula I.

1,2-Dihydro-3-hydroxy-N-(5-indolinyl)pyrido(1,2-a) benzimidazole-4-carboxamide, i.e., where R, $R_2$, $R_3$, and $R_4$ are hydrogen, $R_1$ is 5-indolinyl, Y is NH, X is oxygen, and n=0 in formula I.

1,2-Dihydro-N-(3-dimethylaminophenyl)-3-hydroxy-pyrido(1,2-a)benzimidazole-4-carboxamide, i.e., where R, $R_2$, $R_3$, and $R_4$ are hydrogen, $R_1$ is 3-dimethylaminophenyl, Y is NH, X is oxygen, and n=0 in formula I.

N-(2,6-Difluorophenyl)-1,2-dihydro-3-hydroxy-pyrido(1,2-a)benzimidazole-4-carboxamide, i.e., where R, $R_2$, $R_3$, and $R_4$ are hydrogen, $R_1$ is 2,6-difluorophenyl, Y is NH, X is oxygen, and n=0 in formula I.

N-Cyclohexyl-1,2-dihydro-3-hydroxy-7-methoxypyrido(1,2-a)benzimidazole-4-carboxamide, i.e., where R is 7-methoxy, $R_2$, $R_3$ and $R_4$ are hydrogen, $R_1$ is cyclohexyl, Y is NH, X is oxygen, and n=0 in formula I.

N-Butyl-1,2-Dihydro-3-hydroxy-pyrido(1,2-a) benzimidazole-4-carboxamide, i.e., where R, $R_2$, $R_3$, and $R_4$ are hydrogen, $R_1$ is butyl, Y is NH, X is oxygen, and n=0 in formula I.

1,2-Dihydro-3-hydroxy-N-(4-pyrimidinyl)pyrido (1,2-a) benzimidazole-4-carboxamide, i.e., where R, $R_2$, $R_3$, and $R_4$ are hydrogen, $R_1$ is pyrimidinyl, Y is NH, X is oxygen, and n=0 in formula I.

N-Cyclopropyl-1,2-dihydro-3-hydroxy-pyrido(1,2-a) benzimidazole-4-carboxamide, i.e., where R, $R_2$, $R_3$, and $R_4$ are hydrogen, $R_1$ is cyclopropyl, Y is NH, X is oxygen, and n=0 in formula I.

N-(4-Bromophenyl)-1,2-dihydro-3-hydroxy-pyrido(1,2-a) benzimidazole-4-carboxamide, i.e., where R, $R_2$, $R_3$, and $R_4$ are hydrogen, $R_1$ is 4-bromophenyl, Y is NH, X is oxygen, and n=0 in formula I.

1,2-Dihydro-N-(4-fluorophenyl)-3-hydroxy-pyrido(1,2-a) benzimidazole-4-carboxamide, i.e., where R, $R_2$, $R_3$, and $R_4$ are hydrogen, $R_1$ is 4-fluorophenyl, Y is NH, X is oxygen, and n=0 in formula I.

1,2-Dihydro-3-hydroxy-N-(2-pyrimidinyl)pyrido(1,2-a) benzimidazole-4-carboxamide, i.e., where R, $R_2$, $R_3$, and $R_4$ are hydrogen, $R_1$ is 2-pyrimidinyl, Y is NH, X is oxygen, and n=0 in formula I.

N-(2-Aminophenyl)-1,2-dihydro-3-hydroxy-pyrido(1,2-a) benzimidazole-4-carboxamide, i.e., where R, $R_2$, $R_3$, and $R_4$ are hydrogen, $R_1$ is 2-aminophenyl, Y is NH, X is oxygen, and n=0 in formula I.

1,2-Dihydro-3-hydroxy-N-(6-indazolyl)pyrido(1,2-a) benzimidazole-4-carboxamide, i.e., where R, $R_2$, $R_3$, and $R_4$ are hydrogen, $R_1$ is 6-indazolyl, Y is NH, X is oxygen, and n=0 in formula I.

1,2-Dihydro-3-hydroxy-N-(1,2,4-triazin-3-yl)pyrido(1,2-a) benzimidazole-4-carboxamide, i.e., where R, $R_2$, $R_3$, and R$_4$ are hydrogen, R$_1$ is 1,2,4-triazin-3-yl, Y is NH, X is oxygen, and n=0 in formula I.

1,2-Dihydro-3-hydroxy-N-(5-indazolyl)pyrido(1,2-a) benzimidazole-4-carboxamide, i.e., where R, R$_2$, R$_3$, and R$_4$ are hydrogen, R$_1$ is 5-indazolyl, Y is NH, X is oxygen, and n=0 in formula I.

N-(7-Benzofuranyl)-1,2-dihydro-3-hydroxy-pyrido(1,2-a) benzimidazole-4-carboxamide, i.e., where R, R$_2$, R$_3$, and R$_4$ are hydrogen, R is 7-benzofuranyl, Y is NH, X is oxygen, and n=0 in formula I.

1,2-Dihydro-3-hydroxy-N-(4-pyridylmethyl)pyrido(1,2-a) benzimidazole-4-carboxamide, i.e., where R, R$_2$, R$_3$, and R$_4$ are hydrogen, R$_1$ is 4-pyridylmethyl, Y is NH, X is oxygen, and n=0 in formula I.

1,2-Dihydro-3-hydroxy-N-(3-methylthiopyridin-4-yl) pyrido(1,2-a)benzimidazole-4-carboxamide, i.e., where R, R$_2$, R$_3$, and R$_4$ are hydrogen, R$_1$ is 2-methylthiopyridin-4-yl, Y is NH, X is oxygen, and n=0 in formula I.

1,2-Dihydro-3-hydroxy-N-(3-methylisoxazol-5-yl)-pyrido (1,2-a)benzimidazole-4-carboxamide, i.e., where R, R$_2$, R$_3$, and R$_4$ are hydrogen, R$_1$ is 3-methylisoxazol-5-yl, Y is NH, X is oxygen, and n=0 in formula I.

N-(2-Chloropyridin-3-yl)-1,2-dihydro-3-hydroxy-pyrido(1, 2-a)benzimidazole-4-carboxamide, i.e., where R, R$_2$, R$_3$, and R$_4$ are hydrogen, R$_1$ is 2-chloropyridin-3-yl, Y is NH, X is oxygen, and n=0 in formula I.

N-(4-Diethylaminophenyl)-1,2-dihydro-3-hydroxy-pyrido (1,2-a)benzimidazole-4-carboxamide, i.e., where R, R$_2$, R$_3$, and R$_4$ are hydrogen, R$_1$ is 4-diethylaminophenyl, Y is NH, X is oxygen, and n=0 in formula I.

N-(6-Benzothiazolyl)-1,2-dihydro-3-hydroxy-pyrido(1,2-a) benzimidazole-4-carboxamide, i.e., where R, R$_2$, R$_3$, and R$_4$ are hydrogen, R$_1$ is 6-benzothiazolyl, Y is NH, X is oxygen, and n=0 in formula I.

N-(3-Chloropyridin-4-yl)-1,2-dihydro-3-hydroxy-pyrido(1, 2-a)benzimidazole-4-carboxamide, i.e., where R, R$_2$, R$_3$, and R$_4$ are hydrogen, R$_1$ is 3-chloropyridin-4-yl, Y is NH, X is oxygen, and n=0 in formula I.

7-Chloro-1,2-dihydro-N-(4-dimethylaminophenyl)-3-hydroxy-pyrido(1,2-a)benzimidazole-4-carboxamide, i.e., where R is 7-chloro, R$_2$, R$_3$ and R$_4$ are hydrogen, R$_1$ is 4-dimethylaminophenyl, Y is NH, X is oxygen, and n=0 in formula I.

7-Chloro-1,2-dihydro-3-hydroxy-N-(phenyl)pyrido(1,2-a) benzimidazole-4-carboxamide, i.e., where R is 7-chloro, R$_2$, R$_3$ and R$_4$ are hydrogen, R$_1$ is phenyl, Y is NH, X is oxygen, and n=0 in formula I.

7-Chloro-1,2-dihydro-3-hydroxy-N-(4-pyridyl)pyrido(1,2-a)benzimidazole-4-carboxamide, i.e., where R is 7-chloro, R$_2$, R$_3$ and R$_4$ are hydrogen, R$_1$ is 4-pyridyl, Y is NH, X is oxygen, and n=0 in formula I.

N-Cyclobutyl-1,2-dihydro-3-hydroxy-pyrido(1,2-a) benzimidazole-4-carboxamide, i.e., where R, R$_2$, R$_3$, and R$_4$ are hydrogen, R$_1$ is cyclobutyl, Y is NH, X is oxygen, and n=0 in formula I.

N-(2-Fluoro-4-dimethylaminophenyl)-1,2-dihydro-3-hydroxy-pyrido(1,2-a)benzimidazole-4-carboxamide, i.e., where R, R$_2$, R$_3$, and R$_4$ are hydrogen, R$_1$ is 2-fluoro-4-dimethylaminophenyl, Y is NH, X is oxygen, and n=0 in formula I.

1,2-Dihydro-3-hydroxy-6-methyl-N-(4-pyridyl)pyrido(1,2-a)benzimidazole-4-carboxamide, i.e., where R is 6-methyl, R$_2$, R$_3$ and R$_4$ are hydrogen, R$_1$ is 4-pyridyl, Y is NH, X is oxygen, and n=0 in formula I.

1,2-Dihydro-3-hydroxy-6-methyl-N-(phenyl)pyrido(1,2-a) benzimidazole-4-carboxamide, i.e., where R is 6-methyl, R$_2$, R$_3$ and R$_4$ are hydrogen, R$_1$ is phenyl, Y is NH, X is oxygen, and n=0 in formula I.

N-(4-Carboxamidophenyl)-1,2-dihydro-3-hydroxy-pyrido (1,2-a)benzimidazole-4-carboxamide, i.e., where R, R$_2$, R$_3$, and R$_4$ are hydrogen, R$_1$ is 4-carboxamidophenyl, Y is NH, X is oxygen, and n=0 in formula I.

1,2-Dihydro-3-hydroxy-N-(pentafluorophenyl)pyrido(1,2-a)benzimidazole-4-carboxamide, i.e., where R, R$_2$, R$_3$, and R$_4$ are hydrogen, R$_1$ is pentafluorophenyl, Y is NH, X is oxygen, and n=0 in formula I.

N-(2,4-Difluorophenyl)-1,2-dihydro-3-hydroxy-pyrido(1,2-a)benzimidazole-4-carboxamide, i.e., where R, R$_2$, R$_3$, and R$_4$ are hydrogen, R$_1$ is 2,4-difluorophenyl, Y is NH, X is oxygen, and n=0 in formula I.

1,2-Dihydro-N-(2-fluorophenyl)-3-hydroxy-6-methyl-pyrido(1,2-a)benzimidazole-4-carboxamide, i.e., where R is 6-methyl, R$_2$, R$_3$ and R$_4$ are hydrogen, R$_1$ is 2-fluorophenyl, Y is NH, X is oxygen, and n=0 in formula I.

Phenyl-1,2-dihydro-3-hydroxy-pyrido(1,2-a) benzimidazole-4-carboxylate, i.e., where R, R$_2$, R$_3$, and R$_4$ are hydrogen, R$_1$ is phenyl, Y is oxygen, X is oxygen, and n=0 in formula I.

Phenyl-1,2-dihydro-3-hydroxy-pyrido(1,2-a) benzimidazole-4-carboxythiolate, i.e., where R, R$_2$, R$_3$, and R$_4$ are hydrogen, R$_1$ is phenyl, Y is sulfur, X is oxygen, and n=0 in formula I.

N-(4-Dimethylaminophenyl)-5-ethyl-3-oxo-1,2,3,5-tetrahydropyrido(1,2-a)benzimidazole-4-carboxamide, i.e., where R, R$_3$, and R$_4$ are hydrogen, R$_2$ is ethyl, R$_1$ is 4-dimethylaminophenyl, Y is NH, X is oxygen, and n=0 in formula I.

N-(4-Dimethylaminophenyl)-5-methyl-3-oxo-1,2,3,5-tetrahydropyrido (1,2-a)benzimidazole-4-carboxamide, i.e., where R, R$_3$, and R$_4$ are hydrogen, R$_2$ is methyl, R$_1$ is 4-dimethylaminophenyl, Y is NH, X is oxygen, and n=0 in formula I.

5-Methyl-3-oxo-N-(4-pyridyl)-1,2,3,5-tetrahydropyrido(1, 2-a)benzimidazole-4-carboxamide, i.e., where R, R$_3$, and R$_4$ are hydrogen, R$_2$ is methyl, R$_1$ is 4-pyridyl, Y is NH, X is oxygen, and n=0 in formula I.

5-Benzyl-3-oxo-N-phenyl-1,2,3,5-tetrahydropyrido(1,2-a) benzimidazole-4-carboxamide, i.e., where R, R$_3$, and R$_4$ are hydrogen, R$_2$ is benzyl, R$_1$ is phenyl, Y is NH, X is oxygen, and n=0 in formula I.

5-Benzyl-N-(2-fluorophenyl)-3-oxo-1,2,3,5-tetrahydropyrido(1,2-a)benzimidazole-4-carboxamide, i.e., where R, R$_3$, and R$_4$ are hydrogen, R$_2$ is benzyl, R$_1$ is 2-fluorophenyl, Y is NH, X is oxygen, and n=0 in formula I.

5-Benzyl-N-(2,4-difluorophenyl)-3-oxo-1,2,3,5-tetrahydropyrido(1,2-a)benzimidazole-4-carboxamide, i.e., where R, R$_3$, and R$_4$ are hydrogen, R$_2$ is benzyl, R$_1$ is 2,4-difluorophenyl, Y is NH, X is oxygen, and n=0 in formula I.

N-(2-fluorophenyl)-3-oxo-5-propyl-1,2,3,5-tetrahydropyrido(1,2-a)benzimidazole-4-carboxamide, i.e., where R, R$_3$, and R$_4$ are hydrogen, R$_2$ is propyl, R$_1$ is 2-fluorophenyl, Y is NH, X is oxygen, and n=0 in formula I.

N-(2,4-difluorophenyl)-3-oxo-5-propyl-1,2,3,5-tetrahydropyrido(1,2-a)benzimidazole-4-carboxamide, i.e., where R, R$_3$, and R$_4$ are hydrogen, R$_2$ is propyl, R$_1$ is 2,4-difluorophenyl, Y is NH, X is oxygen, and n=0 in formula I.

3-Hydroxy-N-phenylpyrido(1,2-a)benzimidazole-4-carboxamide, i.e., where R and R$_2$ are hydrogen, R$_3$ and $R_4$ are a double bond, $R_1$ is phenyl, Y is NH, X is oxygen, and n=0 in formula I.

N-(2-Fluorophenyl)-3-hydroxy-pyrido(1,2-a)benzimidazole-4-carboxamide, i.e., where R and $R_2$ are hydrogen, $R_3$ and $R_4$ are a double bond, $R_1$ is 2-fluorophenyl, Y is NH, X is oxygen, and n=0 in formula I.

N-(2,6-Difluorophenyl)-3-hydroxy-pyrido(1,2-a)benzimidazole-4-carboxamide, i.e., where R and $R_2$ are hydrogen, $R_3$ and $R_4$ are a double bond, $R_1$ is 2,6-difluorophenyl, Y is NH, X is oxygen, and n=0 in formula I.

5-Methyl-3-oxo-N-(phenyl)-3,5-dihydropyrido(1,2-a)benzimidazole-4-carboxamide, i.e., where R is hydrogen, $R_3$ and $R_4$ are a double bond, $R_2$ is methyl, $R_1$ is phenyl, Y is NH, X is oxygen, and n=0 in formula I.

1,2-Dihydro-N-(3-fluoropyridin-4-yl)-3-hydroxypyrido(1,2-a)benzimidazole-4-carboxamide, i.e., where R, $R_2$, $R_3$ and $R_4$ are hydrogen, $R_1$ is 3-fluoropyridin-4-yl, Y is NH, X is oxygen, and n=0 in formula I.

1,2-Dihydro-N-(2,5-difluorophenyl)-3-hydroxypyrido(1,2-a)benzimidazole-4-carboxamide, i.e., where R, $R_2$, $R_3$ and $R_4$ are hydrogen, $R_1$ is 2,5-difluorophenyl, Y is NH, X is oxygen, and n=0 in formula I.

1,2-Dihydro-3-hydroxy-N-(2-imidazolyl)-pyrido(1,2-a)benzimidazole-4-carboxamide, i.e., where R, $R_2$, $R_3$ and $R_4$ are hydrogen, $R_1$ is 2-imidazole, Y is NH, X is oxygen, and n=0 in formula I.

1,2-Dihydro-3-hydroxy-N-(2-methylpyridin-4-yl)-pyrido(1,2-a)benzimidazole-4-carboxamide, i.e., where R, $R_2$, $R_3$ and $R_4$ are hydrogen, $R_1$ is 3-methylpyridin-4-yl, Y is NH, X is oxygen, and n=0 in formula I.

1,2-Dihydro-3-hydroxy-N-methyl-pyrido(1,2-a)benzimidazole-4-carboxamide, i.e., where R, $R_2$, $R_3$ and $R_4$ are hydrogen, $R_1$ is methyl, Y is NH, X is oxygen, and n=0 in formula I.

1,2-Dihydro-N-(2-bromo-4,6-difluorophenyl)-3-hydroxypyrido(1,2-a)benzimidazole-4-carboxamide, i.e., where R, $R_2$, $R_3$ and $R_4$ are hydrogen, $R_1$ is 2-bromo-4,6-difluorophenyl, Y is NH, X is oxygen, and n=0 in formula I.

1,2-Dihydro-3-hydroxy-N-(1-methylethyl)-pyrido(1,2-a)benzimidazole-4-carboxamide, i.e., where R, $R_2$, $R_3$ and $R_4$ are hydrogen, $R_1$ is 1-methylethyl, Y is NH, X is oxygen, and n=0 in formula I.

7-Chloro-1,2-dihydro-3-hydroxy-N-(2,4,6-trifluorophenyl)-pyrido(1,2-a)benzimidazole-4-carboxamide, i.e., where R is 7-chloro, $R_2$, $R_3$ and $R_4$ are hydrogen, $R_1$ is 2,4,6-trifluorophenyl, Y is NH, X is oxygen, and n=0 in formula I.

1,2-Dihydro-7-fluoro-3-hydroxy-N-(4-pyridyl)-pyrido(1,2-a)benzimidazole-4-carboxamide, i.e., where R is 7-fluoro, $R_2$, $R_3$ and $R_4$ are hydrogen, $R_1$ is 4-pyridyl, Y is NH, X is oxygen, and n=0 in formula I.

1,2-Dihydro-7-fluoro-3-hydroxy-N-(2,4,6-trifluorophenyl)-pyrido(1,2-a) benzimidazole-4-carboxamide, i.e., where R is 7-fluoro, $R_2$, $R_3$ and $R_4$ are hydrogen, $R_1$ is 2,4,6-trifluorophenyl, Y is NH, X is oxygen, and n=0 in formula I.

1,2-Dihydro-7-fluoro-3-hydroxy-N-(2-fluorophenyl)-pyrido(1,2-a)benzimidazole-4-carboxamide, i.e., where R is 7-fluoro, $R_2$, $R_3$ and $R_4$ are hydrogen, $R_1$ is 2-fluorophenyl, Y is NH, X is oxygen, and n=0 in formula I.

1,2-Dihydro-N-(2,6-difluorophenyl)-7-fluoro-3-hydroxy-pyrido(1,2-a)benzimidazole-4-carboxamide, i.e., where R is 7-fluoro, $R_2$, $R_3$ and $R_4$ are hydrogen, $R_1$ is 2,6-difluorophenyl, Y is NH, X is oxygen, and n=0 in formula I.

1,2-Dihydro-7-fluoro-3-hydroxy-N-(3-fluoropyridin-4-yl)-pyrido(1,2-a)benzimidazole-4-carboxamide, i.e., where R is 7-fluoro, $R_2$, $R_3$ and $R_4$ are hydrogen, $R_1$ is 2-fluoropyridin-4-yl, Y is NH, X is oxygen, and n=0 in formula I.

1,2-Dihydro-N-(2,4-difluorophenyl)-7-fluoro-3-hydroxy-pyrido(1,2-a)benzimidazole-4-carboxamide, i.e., where R is 7-fluoro, $R_2$, $R_3$ and $R_4$ are hydrogen, $R_1$ is 2,4-difluorophenyl, Y is NH, X is oxygen, and n=0 in formula I.

1,2-Dihydro-N-(2,6-dichlorophenyl)-7-fluoro-3-hydroxy-pyrido(1,2-a)benzimidazole-4-carboxamide, i.e., where R is 7-fluoro, $R_2$, $R_3$ and $R_4$ are hydrogen, $R_1$ is 2,6-dichlorophenyl, Y is NH, X is oxygen, and n=0 in formula I.

7-Chloro-1,2-dihydro-3-hydroxy-N-(2-fluorophenyl)-pyrido(1,2-a)benzimidazole-4-carboxamide, i.e., where R is 7-chloro, $R_2$, $R_3$ and $R_4$ are hydrogen, $R_1$ is 2-fluorophenyl, Y is NH, X is oxygen, and n=0 in formula I.

7-Chloro-1,2-dihydro-3-hydroxy-N-(2,6-difluorophenyl)-pyrido(1,2-a)benzimidazole-4-carboxamide, i.e., where R is 7-chloro, $R_2$, $R_3$ and $R_4$ are hydrogen, $R_1$ is 2,6 difluorophenyl, Y is NH, X is oxygen, and n=0 in formula I.

1,2-Dihydro-3-hydroxy-N-(4-(2-dimethylaminoethyl)phenyl)-pyrido(1,2-a)benzimidazole-4-carboxamide, i.e., where R, $R_2$, $R_3$ and $R_4$ are hydrogen, $R_1$ is 4-(2-dimethylaminoethyl)phenyl, Y is NH, X is oxygen, and n=0 in formula I.

1,2-Dihydro-N-(2-fluoropyridin-3-yl)-3-hydroxypyrido(1,2-a)benzimidazole-4-carboxamide, i.e., where R, $R_2$, $R_3$ and $R_4$ are hydrogen, $R_1$ is 2-fluoropyridin-3-yl, Y is NH, X is oxygen, and n=0 in formula I.

2,5-Dimethyl-3-oxo-N-(2-fluorophenyl)-1,2,3,5-tetrahydropyrido(1,2-a)benzimidazole-4-carboxamide, i.e., where $R_1$, and $R_3$, are hydrogen, $R_2$ and $R_4$ are methyl, $R_1$ is 2-fluorophenyl, Y is NH, X is oxygen, and n=0 in formula I.

5-Ethyl-3-oxo-N-(4-pyridyl)-1,2,3,5-tetrahydropyrido(1,2-a)benzimidazole-4-carboxamide, i.e., where R, $R_3$, and $R_4$ are hydrogen, $R_2$ is ethyl, $R_1$ is 4-pyridyl, Y is NH, X is oxygen, and n=0 in formula I.

2,5-Dimethyl-3-oxo-N-phenyl-1,2,3,5-tetrahydropyrido(1,2-a)benzimidazole-4-carboxamide, i.e., where R, and $R_3$, are hydrogen, $R_2$ and $R_4$ are methyl, $R_1$ is phenyl, Y is NH, X is oxygen, and n=0 in formula I.

5-Methyl-3-oxo-N-(2,4,6-trifluorophenyl)-1,2,3,5-tetrahydropyrido(1,2-a)benzimidazole-4-carboxamide, i.e., where R, $R_3$, and $R_4$ are hydrogen, $R_2$ is methyl, $R_1$ is 2,4,6-trifluorophenyl, Y is NH, X is oxygen, and n=0 in formula I.

5-Propyl-3-oxo-N-phenyl-1,2,3,5-tetrahydropyrido(1,2-a)benzimidazole-4-carboxamide, i.e., where R, $R_3$,and $R_4$ are hydrogen, $R_2$ is n-propyl, $R_1$ is phenyl, Y is NH, X is oxygen, and n=0 in formula I.

5-Propyl-3-oxo-N-(2,4,6-trifluorophenyl)-1,2,3,5-tetrahydropyrido(1,2-a)benzimidazole-4-carboxamide, i.e., where R, $R_3$, and $R_4$ are hydrogen, $R_2$ is n-propyl, $R_1$ is 2,4,6-trifluorophenyl, Y is NH, X is oxygen, and n=0 in formula I.

N-(2-fluorophenyl)-6-methyl-4-oxo-1,2,3,4-tetrahydro-6H-azepino(1,2-a)benzimidazole-5-carboxamide, i.e., where R, $R_3$, and $R_4$ are hydrogen, $R_2$ is methyl, $R_1$ is 2-fluorophenyl, Y is NH, X is oxygen, n=1, and A is methylene in formula I.

6-Benzyl-N-(2-fluorophenyl)-4-oxo-1,2,3,4-tetrahydro-6H-azepino(1,2-a)benzimidazole-5-carboxamide, i.e., where R, $R_3$, and $R_4$ are hydrogen, $R_2$ is benzyl, $R_1$ is 2-fluorophenyl, Y is NH, X is oxygen, n=1, and A is methylene in formula I.

6-Benzyl-N-(4-pyridyl)-4-oxo-1,2,3,4-tetrahydro-6H-azepino(1,2-a)benzimidazole-5-carboxamide, i.e., where R, $R_3$, and $R_4$ are hydrogen, $R_2$ is benzyl, $R_1$ is 4-pyridyl, Y is NH, X is oxygen, n=1, and A is methylene in formula I.

N-(2-Fluorophenyl)-4-oxo-1,2,3,4-tetrahydro-6H-azepino(1,2-a)benzimidazole-5-carboxamide, i.e., where R, $R_2$, $R_3$, and $R_4$ are hydrogen, $R_1$ is 2-fluorophenyl, Y is NH, X is oxygen, n=1, and A is methylene in formula I.

4-Oxo-N-phenyl-1,2,3,4-tetrahydro-6H-azepino(1,2-a)benzimidazole-5-carboxamide, i.e., where R, $R_2$, $R_3$, and $R_4$ are hydrogen, $R_1$ is phenyl, Y is NH, X is oxygen, n=1, and A is methylene in formula I.

N-(2,4-difluorophenyl)-4-oxo-1,2,3,4-tetrahydro-6H-azepino(1,2-a)benzimidazole-5-carboxamide, i.e., where R, $R_2$, $R_3$, and $R_4$ are hydrogen, $R_1$ is 2,4-difluorophenyl, Y is NH, X is oxygen, n=1, and A is methylene in formula I.

4-Oxo-N-(4-pyridyl)-1,2,3,4-tetrahydro-6H-azepino(1,2-a)benzimidazole-5-carboxamide, i.e., where R, $R_2$, $R_3$, and $R_4$ are hydrogen, $R_1$ is 4-pyridyl, Y is NH, X is oxygen, n=1, and A is methylene in formula I.

6-Methyl-4-oxo-1,2,3,4-tetrahydro-N-(2,4,6-trifluorophenyl)-6H-azepino(1,2-a)benzimidazole-5-carboxamide, i.e., where R, $R_3$, and $R_4$ are hydrogen, $R_2$ is methyl, $R_1$ is 2,4,6-trifluorophenyl, Y is NH, X is oxygen, n=1, and A is methylene in formula I.

When compounds contain a basic moiety, acid addition salts may be prepared and may be chosen from hydrochloric, hydrobromic, hydroiodic, perchloric, sulfuric, nitric, phosphoric, acetic, propionic, glycolic, lactic, pyruvic, oxalic, malonic, succinic, maleic, fumaric, malic, tartaric, citric, benzoic, cinnamic, mandelic, methanesulfonic, p-toluenesulfonic, cyclohexanesulfamic, salicylic, 2-phenoxybenzoic, 2-acetoxybenzoic, or saccharin, and the like. Such salts can are made by reacting the free base of compounds of formula I with the acid and isolating the salt.

Compounds of formula I can also be treated with a base to prepare the salt of the enolate formed. Such pharmaceutically acceptable salts may include but are not restricted to: alkali metal salts such as sodium or potassium; ammonium salts; monoalkylammonium salts; dialkylammonium salts; trialkylammonium salts; tetraalkylammonium salts; and tromethamine salts.

Hydrates and other solvates of the compound of formula I are also included within the scope of this invention and included within the definition of formula I.

The compounds of formula I are prepared as outlined in the following scheme.

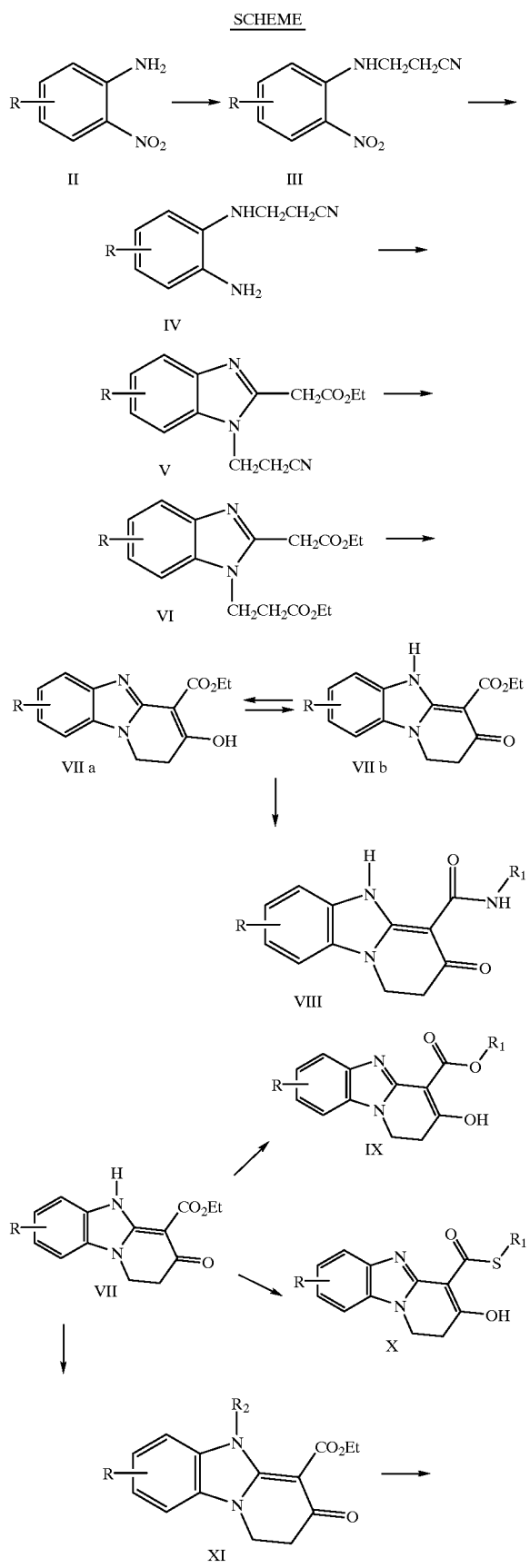

SCHEME

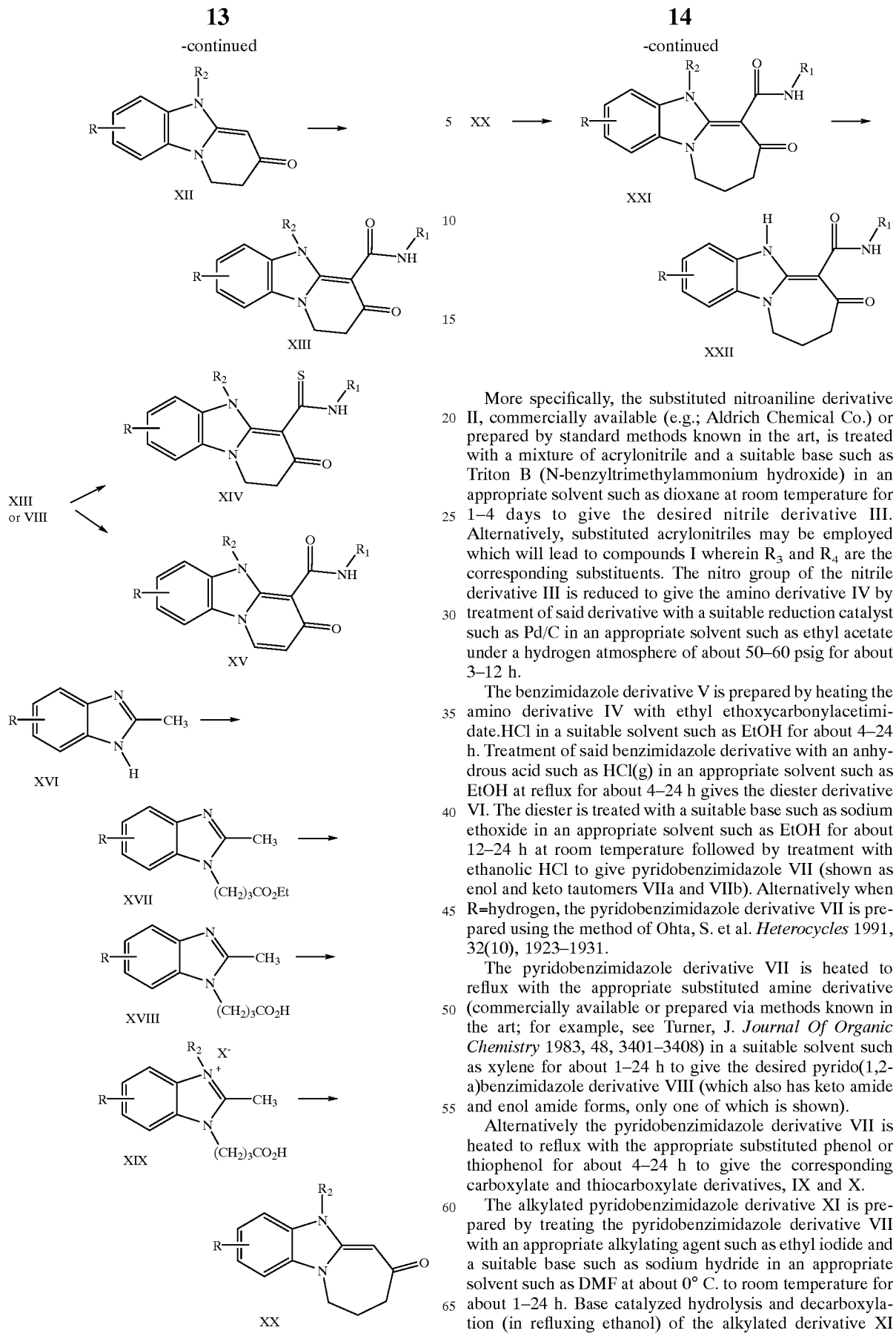

More specifically, the substituted nitroaniline derivative II, commercially available (e.g.; Aldrich Chemical Co.) or prepared by standard methods known in the art, is treated with a mixture of acrylonitrile and a suitable base such as Triton B (N-benzyltrimethylammonium hydroxide) in an appropriate solvent such as dioxane at room temperature for 1–4 days to give the desired nitrile derivative III. Alternatively, substituted acrylonitriles may be employed which will lead to compounds I wherein $R_3$ and $R_4$ are the corresponding substituents. The nitro group of the nitrile derivative III is reduced to give the amino derivative IV by treatment of said derivative with a suitable reduction catalyst such as Pd/C in an appropriate solvent such as ethyl acetate under a hydrogen atmosphere of about 50–60 psig for about 3–12 h.

The benzimidazole derivative V is prepared by heating the amino derivative IV with ethyl ethoxycarbonylacetimidate.HCl in a suitable solvent such as EtOH for about 4–24 h. Treatment of said benzimidazole derivative with an anhydrous acid such as HCl(g) in an appropriate solvent such as EtOH at reflux for about 4–24 h gives the diester derivative VI. The diester is treated with a suitable base such as sodium ethoxide in an appropriate solvent such as EtOH for about 12–24 h at room temperature followed by treatment with ethanolic HCl to give pyridobenzimidazole VII (shown as enol and keto tautomers VIIa and VIIb). Alternatively when R=hydrogen, the pyridobenzimidazole derivative VII is prepared using the method of Ohta, S. et al. *Heterocycles* 1991, 32(10), 1923–1931.

The pyridobenzimidazole derivative VII is heated to reflux with the appropriate substituted amine derivative (commercially available or prepared via methods known in the art; for example, see Turner, J. *Journal Of Organic Chemistry* 1983, 48, 3401–3408) in a suitable solvent such as xylene for about 1–24 h to give the desired pyrido(1,2-a)benzimidazole derivative VIII (which also has keto amide and enol amide forms, only one of which is shown).

Alternatively the pyridobenzimidazole derivative VII is heated to reflux with the appropriate substituted phenol or thiophenol for about 4–24 h to give the corresponding carboxylate and thiocarboxylate derivatives, IX and X.

The alkylated pyridobenzimidazole derivative XI is prepared by treating the pyridobenzimidazole derivative VII with an appropriate alkylating agent such as ethyl iodide and a suitable base such as sodium hydride in an appropriate solvent such as DMF at about 0° C. to room temperature for about 1–24 h. Base catalyzed hydrolysis and decarboxylation (in refluxing ethanol) of the alkylated derivative XI gives the keto derivative XII. Treatment of such keto derivative with a suitable electrophile such as 2-fluorophenyl isocyanate at room temperature for 2–24 h gives the corresponding keto amido derivative XIII.

The thioamido derivative XIV is prepared by heating the corresponding keto amido derivatives XIII or VIII with a suitable sulfur source such as Lawesson's reagent (*Tetrahedron* 1979, 35, 2433) in an appropriate solvent such as toluene at about 80° C. to reflux for about 2–6 h.

Alternatively the keto amido derivatives XIII or VIII are treated with an oxidizing agent such as $MnO_2$ or DDQ (2,3-dichloro-5,6-dicyano-1,4-benzoquinone) at room temperature to reflux for about 5–24 h to give the corresponding oxidized derivative XV.

The keto derivatives XX may be prepared according to the method of M. Okamoto (Japanese Patent Application 61(1986)-190,742). Thus, treatment of an appropriately substituted 2-methylbenzimidazole derivative XVI with ethyl 4-bromobutyrate and an appropriate base such as sodium hydride, in a suitable solvent such as THF at about 0° C. for about 1–4 h gives the desired ester derivative XVII. Alternatively, use of a 4-substituted ethyl 4-bromobutyrate leads to compounds I wherein the "A" is a substituted methine. The ester derivative may be hydrolyzed with a suitable base such as sodium hydroxide in an appropriate solvent such as EtOH followed by aqueous HCl to give the acid derivative XVIII.

The acid derivative XVIII is treated with an alkylating agent such as methyl iodide at about 60° C. to reflux in an appropriate solvent for about 30 min to about 2 h to give the desired alkylated quaternary halide derivative XIX. Treatment of this derivative with carbonyl diimidazole followed by triethylamine, at room temperature to about 70° C. in a suitable solvent such as acetonitrile gives the desired 6-substituted azepinobenzimidazole derivative XX. Alternatively, when $R_2$=benzyl the 6-benzyl azepinobenzimidazole derivative XX is prepared using the method of Ohta, S. et al. *Chem. Pharm. Bull.* 1990, 38(2), 301–306.

The 6-substituted azepinobenzimidazole derivative XX is treated with a suitable electrophile such as 2-fluorophenyl isocyanate at room temperature for about 2–24 h to give the corresponding amido derivative XXI (Ohta, S. et al. *Chem. Pharm. Bull.* 1991, 39(11), 2787–2792).

To obtain the unsubstituted amido derivative XXII one treats the corresponding 6-benzyl substituted amido derivative XXI with a suitable catalyst such as palladium hydroxide in an appropriate solvent such as EtOH under an atmosphere of hydrogen for 24–48 h.

The compounds of this invention were tested for affinity for the benzodiazepine sites of the GABA-A receptor. Since compounds which bind to this receptor can be useful in treating central nervous system disorders, the compounds were also tested in appropriate screens to evaluate specific activities. The results of the various screens are shown in Tables 1–5. Not all compounds were tested in each of the screens. A blank next to a particular compound indicates that the compound was not tested in that screen.

Benzodiazepine Receptor Binding Assay

Selected compounds, which were prepared according to the experimental details given in the following examples, were tested for binding to the benzodiazepine site of the GABA-A receptor (Williams, M. et al., *J. Pharm. Exper. Therap.* 1988, 248, 89). The ability of the compounds of the invention to inhibit the binding of flunitrazepam to prepared receptors was assessed. For each sample, membranes from ca. 10 mg of tissue were incubated in a $K_2HPO_4$-buffered incubation medium (final concentration=2.0 mL). The concentration of ligand ($^3$H-flunitrazepam) was ca. 3 nM. Samples were incubated 10–20 min at 25° C., after which the membrane material and bound ligand was collected on glass fiber filter sheets using vacuum filtration. The collected material was washed with 10 mM HEPES buffered solution, and the radioactivity associated with each sample was measured by liquid scintillation spectrometry. The binding of the test drug to the receptor was determined by comparing the amount of radiolabeled ligand bound in control samples to the amount of ligand bound in the presence of the drug. Concentration-response data were analyzed in a variety of ways. The $IC_{50}$ was usually calculated by transforming the data to a log-logit format, then performing a linear regression analysis. This procedure provides a Hill coefficient as well as the $IC_{50}$ value. The $IC_{50}$ value, for all tested compounds is listed in Tables 1–5. An $IC_{50}$ value of over 10,000 for a particular compound indicates that the compound was not active in this screen. This screen is a general screen and compounds active in this screen are considered active in treating one or more disorders of the central nervous system.

Assay to Measure the Suppression of Anxiety in the Adult Male Rat

The anxiolytic activity of selected compounds of the invention was assessed by determining their ability to release (disinhibit) behavior that had been suppressed by punishment (Vogel, J. R. et al. *Psychopharmacology* 1971, 21, 1). Male rats were deprived of water for 48 hours and were deprived of food for 24 hours prior to testing. After the first 24 hours of water deprivation, they were placed in the conflict chamber for a training period; wherein, they were allowed 200 unpunished licks from a bottle containing tap water. The experiment was run the next day. At the expected time of peak activity, the animals were placed in the chamber and allowed access to tap water. If they failed to drink, the experiment was terminated in 5 min, and animals were evaluated for signs of CNS depression. Their first lick initiates a 3-min test session. Subsequently, every 20th lick was punished by a 0.2-s shock delivered via the stainless-steel drinking-tube. Vehicle-treated control animals generally were willing to accept a median number of 3 to 8 shocks per test session. Animals treated with an active anxiolytic drug tolerated significantly more shocks than control animals. The Wilcoxon rank-sum test (Mann-Whitney U-test) was used to test for an increase ($p<0.05$, 1-tailed) in the median number of shocks in drug-treated groups, compared to a concurrently run vehicle-treated group. The biological assay is considered to be valid if the effects of a known anxiolytic (positive control) are detected, within the same experiment. A compound was considered active if there is a significant difference in the median number of shocks tolerated between the drug-treated group and the control group. The minimum effective doses (MED) for the active compounds of the invention are listed in Tables 1 to 5. The MED was defined as the minimum dose of the drug-treatment as analyzed using the Wilcoxon rank-sum test (SAS; Statistical Analysis System, version 5.16). If the MED value is greater than 10, an active dose of the compound being tested had not been determined.

Assay to Determine the Suppression of Metrazol-Induced Convulsions in Adult Male Rats and Mice Selected compounds of the invention were tested for their ability to reduce metrazol-induced convulsions in mice (Swinyard, E. A. *J. Am. Pharm Assoc.* 1949, 38, 201). Male CD₁ mice, were fasted at least 16 hours, were divided into equal groups and test compounds or vehicle were administered parenterally. Water was not withheld except during the period of observations. At the time of suspected peak activity, anti-pentylenetetrazol (anti-metrazol) activity was evaluated by the subcutaneous administration of the $CD_{90}$ dose of metrazol (the dose of metrazol was determined from the dose-response curve producing clonic convulsions in 90% of animals that received the corresponding vehicle for this experiment). Metrazol was dissolved in 0.9% sodium chloride solution, and its dose volume was 10 ml/kg. Animals were housed individually for observation of clonic convulsions, tonic convulsions and death for a period of 30 min. Test compounds that blocked the clonic seizure component of the convulsion in at least 50% of the animals were considered active. The biological assay was considered to be valid if the effects of a known anticonvulsant (positive control) were detected, within the same experiment. Activity was reported as percent reduction of clonic convulsions from the vehicle group. The $ED_{50}$ values of active compounds were calculated by the method of probits (Finney, D. J. 1971. Probit Analysis. London: Cambridge University Press) and are listed in Tables 1 to 5. An $ED_{50}$ value of greater than 30 indicates that an active dose for the compound being tested had not been determined. Compounds active in this screen are considered active anticonvulsion/antiepileptic agents.

Horizontal Screen Test for Motor Coordination

Some of the compounds of the invention were tested for their ability to act as general CNS agents and particularity as skeletal muscle relaxants and hypnotics/sedatives (Coughenour, L. L. et al. *Pharm. Biochem. Behav.* 1977, 6, 351). Male CD₁ mice, fasted for at least 16 hours but allowed access to water except during the period of observation, were placed on a horizontally-held screen (mesh size ¼", wire diameter approximately 1.0 mm). The screen was inverted and mice which successfully climb to the top side of the screen within one minute were selected for testing. Selected mice were weighed and divided into equal groups. Test compounds or vehicle were administered to those mice parenterally. At a pre-determined interval (or intervals) after administration, the animals were tested for their ability to climb to the top side of the inverted screen (pass the test). Activity is reported as the percent reduction in the number of animals that pass the test in each treatment group relative to the corresponding vehicle-treated group. Percent Reduction=100×([Percent Pass in Vehicle Group]−[Percent Pass in Test Group]/Percent Pass in Vehicle Group). Test compounds which produce a 50% or greater reduction in the number passing the test were considered active. $ED_{50}$ values of the active compounds were calculated by the method of probits (Finney, D. J. 1971. Probit Analysis. London: Cambridge University Press) and are listed in Tables 1 to 5. An $ED_{50}$ value of greater than 300 indicates that an active dose for the compound being tested had not been determined.

Horizontal Screen Test for Determining Benzodiazepine Antagonism

Some of the compounds of the invention were tested for their ability to antagonize the locomotor discoordinating property of chlordiazepoxide. Male CD₁ mice, fasted for at least 16 hours but allowed access to water except during the period of observation, were placed on a horizontally-held screen (mesh size ¼", wire diameter approximately 1.0 mm). The screen was inverted and mice which successfully climb to the top side of the screen within one minute were selected for testing. Selected mice were weighed and divided into equal groups. Test compounds or vehicle were administered to those mice parenterally at the same time as chlordrazepoxide (28 mg/kg, sc). At a pre-determined interval (or intervals) after administration, the animals were tested for their ability to climb to the top side of the inverted screen (pass the test). Activity is reported as the percent antagonism of the number of animals that fail the test in each treatment group relative to the corresponding chlordiazepoxide-treated group. Percent Antagonism =100×[(Percent Fail in Chlordiazepoxide Group)−(Percent Fail in Test Group)/Percent Fail in Chlordiazepoxide Group]. Since this dose of chlordiazepoxide typically impairs the ability of all animals to pass this test, compounds which prevent impairment in any proportion of the tested animals were considered active. The percent antagonism values for the compounds of the present invention that were tested are as follows: CP 113=0, CP 53=0, CP 59=0,CP 102=0,CP 11=17,CP 7=17,CP 8=17,CP 9=30,CP 10=30, CP 11=92, CP 12=92, CP 13=100. Compounds having values above 0 were considered active as agents for treating drug overdoses, particularly overdoses of benzodiazepine.

TABLE 1

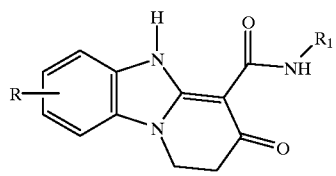

| CP # | R₁ | R | IC₅₀ (nM) | Conflict (ip) MED (mg/kg) | Metrazol (ip) ED₅₀ (mg/kg) | Horiz. Screen ED₅₀ (mg/kg) |
|---|---|---|---|---|---|---|
| 1 | Ph | H | 9.1 | 10 | 3 | |
| 2 | PhCH₂CH₂ | H | 280 | >10 | 10–30 | |
| 3 | 2-thiazole | H | 43 | 10 | 30 | |
| 4 | 4-MeOPh | H | 41 | 10 | 3 | |
| 5 | 4-ClPh | H | 620 | 1 | 5 | |
| 6 | 3-ClPh | H | 120 | >10 | >30 | |
| 7 | c-C₆H₁₁ | H | 140 | 10 | 10 | |
| 8 | 3,4-(MeO)2Ph | H | 32 | >10 | >30 | |
| 9 | 4-NO₂Ph | H | >10,000 | >10 | >300 | 300 |

TABLE 1-continued

| CP # | R₁ | R | IC$_{50}$ (nM) | Conflict (ip) MED (mg/kg) | Metrazol (ip) ED$_{50}$ (mg/kg) | Horiz. Screen ED$_{50}$ (mg/kg) |
|---|---|---|---|---|---|---|
| 10 | 4-HOPh | H | 46 | 10 | >30 | |
| 11 | 3-pyridyl | H | 51 | 10 | 5 | |
| 12 | Ph | 7-OMe | 40 | >10 | 3 | |
| 13 | 4-MeOPh | 7-OMe | 210 | >10 | 10–30 | |
| 14 | 2,6-Cl$_2$Ph | H | 320 | >10 | 30 | |
| 15 | 3-(CF$_3$)Ph | H | 300 | >10 | >10 | |
| 16 | Ph | 7-CF$_3$ | 960 | | | |
| 17 | 4-(C$_4$H$_9$)Ph | H | >10,000 | | >10 | 300 |
| 18 | 4-NH$_2$Ph | H | 13,000 | >10 | 3 | |
| 19 | 2,6-Me$_2$Ph | H | 7700 | >10 | >30 | 300 |
| 20 | 2-FPh | H | 1.7 | 1 | 0.1 | |
| 21 | 3-MeOPh | H | 26 | 5 | 0.3 | |
| 22 | 2-pyridyl | H | 59 | 10 | 10 | |
| 23 | 4-MeSPh | H | 400 | >10 | 10 | |
| 24 | 4-Me$_2$NPh | H | 270 | 3 | 3 | |
| 25 | 2-ClPh | H | 12 | 10 | 1 | |
| 26 | 2-MeOPh | H | 990 | >10 | >10 | |
| 27 | 4-(EtO$_2$C)Ph | H | >10,000 | <10 | >30 | |
| 28 | 4-(HO$_2$C)Ph | H | >10,000 | 10 | >30 | |
| 29 | H | H | 2400 | 10 | >3 | |
| 30 | 5-indolyl | H | 530 | >10 | >30 | |
| 31 | 2-MePh | H | 230 | 10 | >30 | |
| 32 | CH$_2$Ph | H | 38 | >10 | >30 | |
| 33 | 5-indolinyl | H | 54 | 10 | >30 | |
| 34 | 3-Me$_2$NPh | H | 37 | >10 | 4 | |
| 35 | 4-pyridyl | H | 160 | 3 | 2 | |
| 36 | 2,6-F$_2$Ph | H | 2.8 | 0.1 | 1 | |
| 37 | c-C$_6$H$_{11}$ | 7-OMe | 800 | 10 | 10 | |
| 38 | C$_4$H$_9$ | H | 54 | >10 | >10 | |
| 39 | 4-pyrimidinyl | H | 480 | 10 | >10 | |
| 40 | 2-MeSPh | H | 720 | >10 | >10 | |
| 41 | 6-quinolinyl | H | 130 | >10 | >30 | |
| 42 | 1,2,4-triazol-4-yl | H | 2700 | >10 | >10 | 300 |
| 43 | C-C$_3$H$_5$ | H | 16 | >10 | >10 | |
| 44 | 4-BrPh | H | 130 | >10 | 3 | |
| 45 | 4-FPh | H | 430 | 10 | >30 | |
| 46 | 2-pyrimidinyl | H | 54 | 10 | 3 | |
| 47 | 2-NH$_2$Ph | H | 50 | 10 | 3 | |
| 48 | 6-indazolyl | H | 350 | 10 | >30 | |
| 49 | 3-(1,2,4-triazinyl) | H | 54 | >10 | 10 | |
| 50 | 5-indazolyl | H | 96 | 10 | >10 | |
| 51 | 7-benzofuranyl | H | 120 | 10 | >10 | |
| 52 | 4-(2-Cl-pyridyl) | H | 1400 | >10 | >10 | |
| 53 | 2-(1,3,5-triazinyl) | H | 110 | >10 | >10 | |
| 54 | 4-CNPh | H | 13,000 | <10 | >10 | |
| 55 | 4-(tetraF-pyridyl) | H | 350 | >10 | >10 | |
| 56 | 4-(N-Me-pyridyl) | H | 6300 | >10 | >10 | 100 |
| 57 | 4-pyridyl | 7-OMe | 500 | >10 | >10 | |
| 58 | 4-piperidinyl | H | >10,000 | >10 | >10 | 100 |
| 59 | CH$_2$(4-pyridyl) | H | 65 | >10 | >10 | |
| 60 | 4-morpholinyl | H | 3000 | <10 | >10 | |
| 61 | 4-NH$_2$SO$_2$Ph | H | 10,000 | 10 | >10 | |
| 62 | CH$_2$(3-pyridyl) | H | 155 | >10 | >10 | |
| 63 | 2-pyrazinyl | H | 360 | >10 | >10 | |
| 64 | 5-Me-1,3,4-thiadiazol-2-yl | H | 1100 | >10 | >10 | |
| 65 | 5-isoquinolinyl | H | 770 | >10 | 10 | |
| 66 | 4-(3-MeS-pyridyl) | H | 3300 | 10 | 10 | |
| 67 | 4-(3,5-Cl$_2$-2,6-F$_2$pyridyl) | H | 10,000 | 10 | 10 | |
| 68 | 5-(3-Me-isoxazolyl) | H | 54 | >10 | >10 | |
| 69 | 2-thiadiazolyl | H | 300 | >10 | >10 | |
| 70 | 3-(2-Cl-pyridyl) | H | 68 | 10 | 3 | |
| 71 | 4-Et$_2$NPh | H | 1800 | >10 | 3 | |
| 72 | 6-benzothiazolyl | H | 10,000 | <10 | >10 | |
| 73 | 5-benzotriazolyl | H | 160 | >10 | >10 | |
| 74 | 5-CF$_3$-thiadiazolyl | H | 10,000 | >10 | 10 | |
| 75 | 4-(3-Cl-pyridyl) | H | 220 | >10 | 1–10 | |

TABLE 1-continued

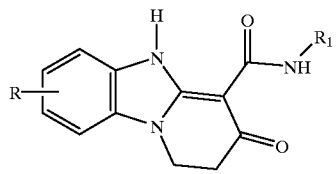

| CP # | R₁ | R | IC$_{50}$ (nM) | Conflict (ip) MED (mg/kg) | Metrazol (ip) ED$_{50}$ (mg/kg) | Horiz. Screen ED$_{50}$ (mg/kg) |
|---|---|---|---|---|---|---|
| 76 | 4-quinaldinyl | H | 10,000 | >10 | 10 | |
| 77 | 4-(3-Me-pyridyl) | H | 7100 | >10 | >10 | |
| 78 | 2-(3,5-(CF$_3$)$_2$pyridyl) | H | >10,000 | 10 | >10 | |
| 79 | 2-MeS-4-Me$_2$N-Ph | H | 660 | >10 | >10 | |
| 80 | 4-Me$_2$NPh | 7-Cl | 220 | >10 | 10 | |
| 81 | Ph | 7-Cl | 66 | 10 | >10 | |
| 82 | 4-pyridyl | 7-Cl | 380 | >10 | 3 | |
| 83 | c-C$_4$H$_7$ | H | 30 | 10 | >30 | |
| 84 | Ph | 8-Cl | 170 | >10 | >10 | |
| 85 | 2-Me-4-Me$_2$NPh | H | 4000 | >10 | 10 | |
| 86 | 2-F-4-Me$_2$NPh | H | 120 | | 1 | |
| 87 | 2-Me$_2$NPh | H | 10,000 | 10 | 10 | |
| 88 | 4-pyridyl | 6-Me | 390 | >10 | 10 | |
| 89 | Ph | 6-Me | 10 | >10 | 1 | |
| 90 | 4-NH$_2$COPh | H | 110 | >10 | >10 | >10 |
| 91 | C$_6$F$_5$ | H | 270 | 10 | 1–10 | |
| 92 | 2,4-F$_2$Ph | H | 10 | >10 | 1 | |
| 93 | 2,4,6-F$_3$Ph | H | 15 | 3 | 1 | |
| 94 | 2-FPh | 6-Me | 96 | <10 | 1 | |
| 95 | 3-FPh | H | 160 | >10 | >10 | >10 |
| 96 | 2,3,4-F$_3$Ph | H | 1500 | >10 | >10 | |
| 97 | 4-(3-F-pyridyl) | H | 53 | 10 | 1 | >10 |
| 98 | 2,5-F$_2$Ph | H | 12 | >30 | >30 | |
| 99 | 2-imidazol | H | 185 | >10 | >30 | |
| 100 | 4-(2-Me-pyridyl) | H | 820 | >10 | >10 | |
| 101 | 2,4,6-Cl$_3$Ph | H | | >10 | >10 | |
| 102 | Me | H | 400 | >10 | >10 | |
| 103 | 2-Br-4,6-F$_2$Ph | H | 1200 | >10 | >10 | |
| 104 | 2,4,6-F$_3$Ph | 7-Cl | 13 | 10 | 1 | |
| 105 | 2-Pr | H | 46 | >10 | >10 | |
| 106 | 4-pyridyl | 7-F | 42 | 3 | 3 | |
| 107 | 2,4,6-F$_3$Ph | 7-F | 3 | 0.3 | 1 | |
| 108 | 2-FPh | 7-F | 2 | 10 | <1 | |
| 109 | 2,6-F$_2$Ph | 7-F | 1.3 | 3 | 0.3 | |
| 110 | 4-(3-F-pyridyl) | 7-F | 12 | | | |
| 111 | 2,4-F$_2$Ph | 7-F | 3.3 | | | |
| 112 | 2,6-Cl$_2$Ph | 7-F | 100 | | | |
| 113 | 2-FPh | 7-Cl | 5 | <10 | 1 | |
| 114 | 2,6-F$_2$Ph | 7-Cl | 6 | 3 | 1 | |
| 115 | 4-(2-Me$_2$NCH$_2$CH$_2$)Ph | H | 110 | 30 | >30 | |
| 116 | 3-(2-F-pyridyl) | H | | >10 | 2 | |

TABLE 2

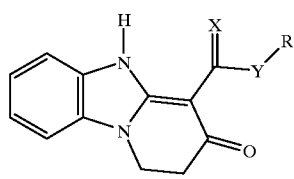

| CP # | R₁ | X | Y | IC$_{50}$ (nM) | Conflict (ip) MED (mg/kg) | Antimetrazol (ip) ED$_{50}$ (mg/kg) |
|---|---|---|---|---|---|---|
| 117 | Ph | S | NH | 360 | >10 | >10 |
| 118 | Ph | O | O | 200 | >10 | 3 |
| 119 | Ph | O | S | 29 | >10 | >30 |

TABLE 3

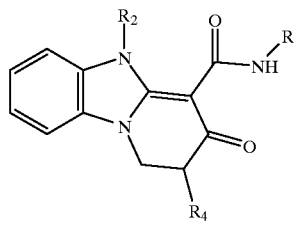

| CP # | $R_1$ | $R_2$ | $R_4$ | $IC_{50}$ (nM) | Conflict MED (mg/kg) | Antimetrazol $ED_{50}$ (mg/kg) |
|---|---|---|---|---|---|---|
| 120 | Ph | Me | H | 6 | <1 | <1 |
| 121 | Ph | Et | H | <0.1 | <1 | <1 |
| 122 | 2-FPh | Me | H | <1 | 0.03 | 0.03 |
| 123 | 2-FPh | Et | H | 2.1 | 0.3 | 0.01 |
| 124 | 4-Me$_2$NPh | Me | H | 29 | 10 | 1–3 |
| 125 | 4-Me$_2$NPh | Et | H | 72 | >10 | 0.3 |
| 126 | 4-pyridyl | Me | H | 230 | <10 | 3 |
| 127 | Ph | Bzl | H | 12 | 10 | 3 |
| 128 | 2-FPh | Bzl | H | 88 | >10 | 1 |
| 129 | 2,4-F$_2$Ph | Bzl | H | 12 | >10 | 1 |
| 130 | 2-FPh | Pr | H | <1.0 | <0.3 | 0.1 |
| 131 | 2,4-F$_2$Ph | Pr | H | 2.6 | <1 | 0.3 |
| 132 | 2-F-Ph | Me | Me | | <10 | 1 |
| 133 | 4-pyridyl | Et | H | 80 | 3 | 3 |
| 134 | Ph | Me | Me | 67 | >10 | 3 |
| 135 | 2-4,6-F$_3$Ph | Me | H | 13 | >10 | 10 |
| 136 | Ph | Pr | H | 2.5 | 10 | 1 |
| 137 | 2,4,6-F$_3$Ph | Pr | H | <100 | >10 | 1 |

TABLE 4

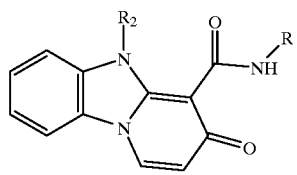

| CP # | $R_1$ | $R_2$ | $IC_{50}$ (nM) | Conflict MED (mg/kg) | Antimetrazol $ED_{50}$ (mg/kg) |
|---|---|---|---|---|---|
| 138 | Ph | H | 24 | 1–10 | 0.5 |
| 139 | 2-FPh | H | 0.23 | 0.1 | 0.3 |
| 140 | 4-pyridyl | H | 260 | >10 | >10 |
| 141 | 2,6-F$_2$Ph | H | <1 | 0.3 | <0.1 |
| 142 | Ph | Me | 45 | <1 | <1 |

TABLE 5

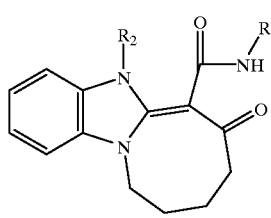

| CP # | $R_1$ | $R_2$ | $IC_{50}$ (nM) | Conflict MED (mg/kg) | Antimetrazol $ED_{50}$ (mg/kg) |
|---|---|---|---|---|---|
| 143 | Ph | H | 104 | 10 | >10 |
| 144 | Ph | Me | 28 | >10 | >10 |
| 145 | Ph | Bzl | 420 | >10 | >10 |

TABLE 5-continued

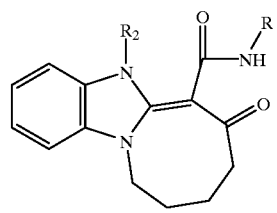

| CP # | $R_1$ | $R_2$ | $IC_{50}$ (nM) | Conflict MED (mg/kg) | Antimetrazol $ED_{50}$ (mg/kg) |
|---|---|---|---|---|---|
| 146 | 2-FPh | H | 3.1 | 10 | 1–10 |
| 147 | 2-FPh | Me | 22 | >10 | >10 |
| 148 | 2-FPh | Bzl | 150 | >10 | >10 |
| 149 | 4-Me$_2$NPh | H | 1120 | >10 | >10 |
| 150 | 4-Me$_2$NPh | Me | 3100 | >10 | >10 |
| 151 | 4-Me$_2$NPh | Bzl | 12400 | >10 | >10 |
| 152 | 4-pyridyl | H | 1460 | <10 | >10 |
| 153 | 4-pyridyl | Me | 2600 | >10 | >10 |
| 154 | 4-pyridyl | Bzl | 6700 | | >10 |
| 155 | 2,4-F$_2$Ph | H | 39 | >10 | 10 |
| 156 | 2,4-F$_2$Ph | Bzl | 330 | >10 | >10 |
| 157 | 2,4,6-F$_3$Ph | Me | 53 | >10 | >10 |

To prepare the pharmaceutical compositions of this invention, one or more compounds or salts thereof, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will preferably contain per dosage unit, e.g., tablet, capsule, powder, injection, teaspoonful and the like, from about 5 to about 500 mg of the active ingredient, although other unit dosages may be employed.

In therapeutic use in treating disorders of the central nervous system in mammals, the compounds of this invention may be administered in an amount of from about 0.2 to 25 mg/kg per day. In therapeutic use as an anxiolytic, the compounds of the invention may be administered in an amount from about 0.2 to 25 mg/kg per day. In therapeutic use as an anticonvulsant/antiepileptic, the compounds of the invention may be administered in an amount from about 0.2 to 25 mg/kg per day. In therapeutic use as an agent for treating benzodiazepine overdoses, the compounds of the invention may be administered in an amount from about 0.2 to 25 mg/kg per day. In therapeutic use as a sedative/hypnotic, a therapeutically effective amount is from about 0.2 to 25 mg/kg per day. As a muscle relaxant about 0.2 to 25 mg/kg per day of the compounds of this invention may be used. Determination of optimum dosages for a particular situation is within the skill of the art.

EXAMPLES

The following examples describe the invention in greater detail and are intended to illustrate the invention, but not to limit it.

Melting point determinations were carried out on a Thomas Hoover or Mel-Temp melting point apparatus and are corrected unless otherwise specified. Each compound has at least two analytical results (elemental analysis, IR, $^1$H NMR, MS) that are consistent with its assigned structures. The infrared spectra (KBr) were recorded on a Nicolet SX 60 FT spectrometer and are expressed in reciprocal centimeters. Nuclear magnetic resonance (NMR) spectra for hydrogen atoms were measured in the indicated solvent with tetramethylsilane (TMS) as the internal standard on a Bruker AM-360 (360 MHz), AM400 (400 MHz), or AT-300 (300 MHz) spectrometer. The values are expressed in parts per million downfield from TMS. The elemental analyses were measured by Atlantic Microlabs (Atlanta, Ga.), Galbraith Labs (Knoxville, Tenn.) or in house and are expressed in percentage by weight of each element per total molecular weight. The mass spectra (MS) were determined on a Finnigan 3300 spectrometer (methane), using desorption chemical ionization techniques. All preparative column chromatography were run using a Waters Prep 500A HPLC (silica gel) employing the appropiate commercially available solvent. Unless otherwise noted, the materials used in the examples were obtained from readily available commercial suppliers or synthesized by standard methods known to anyone skilled in the art of chemical synthesis. The substituents groups, which vary between examples are hydrogen unless otherwise noted.

EXAMPLE 1

N-(4-Pyridyl)-1,2-dihydro-3-hydroxypyrido-(1,2-a) benzimidazole-4-carboxamide (CP #35)

A 40% solution of benzyltrimethylammonium hydroxide in MeOH (50 mL, 0.11 moles) was added to a mixture of 2-nitroaniline (828.3 g, 6 moles) in dioxane (2.5 L) at room temperature. Acrylonitrile (1.2 L, 18.2 moles) was added dropwise to the reaction mixture which was maintained at a temperature of 35–40° C. by means of an external ice bath. The resulting mixture was stirred at room temperature for 4 h and stored at room temperature for 72 h. The pH of the reaction mixture was adjusted to pH 6 by the addition of glacial acetic acid and the resulting orange precipitate was isolated by filtration and washed with several portions of MeOH. The precipitate was dried in vacuo at 40° C. to give the desired nitrile derivative III as a solid: mp 110–112° C. Additional product can be obtained by concentrating the mother liquor and recrystallizing the crude product from methylene chloride and EtOH.

A suspension of the substituted nitrile derivative III (285.4 g, 1.5 moles) and 10% Pd/C (5 g) in EtOAc (1.0 L) was placed in a Parr bottle and pressurized at 50–60 psi for 3–4 h. The resulting mixture was allowed to cool to room temperature (note the elevated temperature came from the heat of the reaction and not from an external source), filtered through Celite and concentrated in vacuo to give the desired amino nitrile derivative IV as a solid.

A solution of ethyl cyanoacetate (1 kg, 8.84 moles) in absolute EtOH (406.6 g, 8.84 moles) was stirred at 5–10° C. under a dry (inert-Ar) atmosphere. Anhydrous HCl gas was bubbled into this mixture for 2.5 h and the resulting mixture was stirred at 5–10° C. for 5–7 h and stored at 4° C. for 16 h. The resulting solid precipitate was isolated, washed with several portions of anhydrous $Et_2O$ and dried in vacuo to give the HCl salt of ethyl ethoxycarbonylacetimidate as a solid: mp 117° C.

A mixture of the aminonitrile derivative IV (725.4 g, 4.5 moles), ethyl ethoxycarbonylacetimidate (880.5 g, 4.5 moles) in absolute EtOH (7 L) was heated at reflux under argon for 4 h and left standing at room temperature for 4 days. The solid precipitate was filtered and washed with EtOH and methylene chloride. Additional methylene chloride (4 L) was added to the filtrate and the the resulting brown solution was concentrated in vacuo to give a grey residue. This residue was partitioned between methylene chloride (6 L) and water (2 L). The resulting organic layer was washed with additional portions of water, dried over $MgSO_4$, filtered and concentrated in vacuo. The residue was recrystallized from isopropanol and the resulting crystals were washed with $Et_2O$ and dried in vacuo to give the cyanoalkyl substituted benzimidazole V as a solid: mp 109–111° C.

Anhydrous HCl(g) was bubbled into a suspension of the cyanoalkyl substituted benzimidazole derivative V (981.4 g, 3.82 moles) and EtOH (11.0 L) at 10–15° C. for 1.5 h. Water (68.7 mL, 3.82 moles) was added and the resulting mixture was heated at reflux for 4 h and stirred at room temperature overnight. The resulting mixture was concentrated in vacuo to a volume of 1.5 L and 6 L of water was added to this mixture. The pH of the mixture was adjusted to pH 8 by the addition of 25% NaOH (aq) and the resulting mixture was extracted with several portions of $Et_2O$. The combined organic extracts were washed with sat'd brine and the resulting solid precipitate was separated and identified as unreacted starting material. The organic extracts were dried over $MgSO_4$ and concentrated in vacuo to give the desired diester VI as a solid: mp (HCl salt): 126–128° C.

Sodium (56.1 g, 2.44 moles) was added to a stirred solution of absolute EtOH (1.42 L) under an argon atmosphere. An additional portion of EtOH (8.3 L) was added to the reaction mixture followed by the dropwise addition of a solution of the diester derivative VI (730.6 g, 2.40 moles) in EtOH (3.0 L). The mixture was stirred overnight at room temperature and the resulting solid precipitate was filtered, washed with additional EtOH and air dried. This solid was suspended in water and the pH was adjusted to 7.9 by the addition of 1 N HCl. This mixture was stirred for 1 h and the resulting solid was isolated (filtered) and air dried to give ethyl 1,2-dihydro-3-hydroxypyrido(1,2-a)benzimidazole-4-carboxylate VII as a solid: mp 233–235° C.

Anal. Calcd for $C_{14}H_{14}N_2O_2$: C, 65.10; H, 5.46; N, 10.86. Found: C, 65.66; H, 5.39; N, 10.97.

The pyridobenzimidazo derivative VII (4.0 g, 15.5 mmol) and 4-aminopyridine (2.82 g, 30.0 mmol) were combined in xylenes (200 mL) and heated at reflux for 6 h in a flask fitted with a Dean Stark trap. The resulting solid was isolated from the cooled reaction mixture and recrystallized from a mixture of methylene chloride and EtOH to give the title compound as a crystalline solid: mp 274–276° C.; MS: 307 $(MH^+)$.

Anal. Calcd for $C_{17}H_{14}N_4O_2$: C, 66.66; H, 4.61; N, 18.29. Found: C, 66.38; H, 4.38; N, 18.29.

The following general procedure was used in the synthesis of the compounds listed in Table 6.

EXAMPLE 2

An appropriately substituted pyridobenzimidazole derivative VII (1 molar equivalent) prepared as in Example 1 and a suitable amine (1.2–2.0 molar equivalents) were combined in xylenes (200 ml) and heated at reflux for 1–6 h in a flask fitted with a Dean Stark trap. The resulting solid was isolated from the reaction mixture and recrystallized from a suitable solvent to give the desired pyridobenzimidazo derivative VIII as a solid. Pharmaceutically acceptable salts of the the desired pyridobenzimidazo derivatives VIII were prepared by treatment of derivatives VIII with the desired mineral or organic acid in a suitable solvent.

TABLE 6

| CP # | $R_1$ | R | m p.° C. | C | H | N | Empirical Formula |
|---|---|---|---|---|---|---|---|
| 1 | Ph | H | 225–227 | 70.28 | 4.88 | 13.59 | C18H15N3O2 |
| 2 | $PhCH_2CH_2$ | H | 182–184 | 71.84 | 5.71 | 12.52 | C20H19N3O2 |
| 3 | 2-thiazole | H | 287–289 (dec) | 57.57 | 4.16 | 17.15 | C15H12N4O2S |
| 4 | 4-MeOPh | H | 196.5–197.5 | 67.91 | 5.11 | 12.55 | C19H17N3O3 |
| 5 | 4-ClPh | H | 258–262 (dec) | 63.45 | 4.17 | 12.37 | C18H14ClN3O2 |
| 6 | 3-ClPh | H | 260–262 | 63.69 | 3.98 | 12.22 | C18H14ClN3O2 |
| 7 | $c$-$C_6H_{11}$ | H | 135–141 | 69.57 | 6.87 | 13.55 | C18H21N3O2 |
| 8 | 3,4-$(MeO)_2$Ph | H | 210.5–211.5 | 65.63 | 5.25 | 11.72 | C20H19N3O4 |
| 9 | 4-$NO_2$Ph | H | 303–310 (dec) | 61.65 | 4.13 | 16.11 | C18H14N4O4 |
| 10 | 4-HOPh | H | 298–301 (dec) | 67.24 | 4.71 | 13.12 | C18H15N3O3 |
| 11 | 3-pyridyl | H | 258–263 (dec) | 66.54 | 4.42 | 18.35 | C17H14N4O2 |
| 12 | Ph | 7-OMe | 246–247 | 68.30 | 5.20 | 12.54 | C19H17N3O3 |
| 13 | 4-MeOPh | 7-OMe | 244–245 | 65.81 | 5.35 | 11.48 | C20H19N3O4 |
| 14 | 2,6-$Cl_2$Ph | H | 134–141 (dec) | 49.17 | 3.71 | 11.17 | C18H13Cl2N3O2 |
| 15 | 3-$(CF_3)$Ph | H | 253.5–255 (dec) | 60.79 | 3.73 | 11.21 | C19H14F3N3O2 |
| 16 | Ph | 7-$CF_3$ | 268–270 | 61.01 | 3.81 | 11.07 | C19H14F3N3O2 |
| 17 | 4-$(C_4H_9)$Ph | H | 181–183 | 73.12 | 6.44 | 11.61 | C22H23N3O2 |
| 18 | 4-$NH_2$Ph | H | 280–281 (dec) | 58.56 | 4.95 | 15.15 | C18H16N4O2.HCl[a] |
| 19 | 2,6-$Me_2$Ph | H | 130–134 (dec) | 72.01 | 5.98 | 12.29 | C20H19N3O2 |
| 20 | 2-FPh | H | 248–250 (dec) | 66.84 | 4.76 | 12.48 | C18H14FN3O2[b] |
| 21 | 3-MeOPh | H | 248–250 | 67.80 | 5.10 | 12.50 | C19H17N3O3 |
| 22 | 2-pyridyl | H | 272–274 (dec) | 66.50 | 4.40 | 18.30 | C17H14N4O2 |
| 23 | 4-MeSPh | H | 219–221 | 64.71 | 4.67 | 11.82 | C19H17N3O2S |
| 24 | 4-$Me_2$NPh | H | 213–214 | 68.55 | 5.74 | 15.93 | C20H20N4O2 |
| 25 | 2-ClPh | H | 228–230 | 63.53 | 4.07 | 12.27 | C18H14ClN3O2 |
| 26 | 2-MeOPh | H | 229–230 | 66.74 | 5.48 | 11.62 | C19H17N3O3[c] |
| 27 | 4-$(EtO_2C)$Ph | H | 239–240 | 66.77 | 4.99 | 11.20 | C21H19N3O4 |
| 28 | 4-$(HO_2C)$Ph | H | 305–306 (bubbles) | 64.23 | 4.42 | 11.86 | C19H15N3O4[d] |
| 29 | H | H | 241–243 | 61.98 | 4.98 | 17.66 | C12H11N3O2[e] |
| 30 | 5-indolyl | H | 320–322 (darkens) | 69.88 | 4.61 | 15.99 | C20H16N4O2 |
| 31 | 2-MePh | H | 219–221 | 71.48 | 5.36 | 13.00 | C19H17N3O2 |
| 32 | $CH_2$Ph | H | 243–244 | 71.67 | 5.28 | 13.06 | C19H17N3O2 |
| 33 | 5-indolinyl | H | 237–240 | 68.32 | 4.99 | 15.70 | C20H18N4O2[f] |
| 34 | 3-$Me_2$NPh | H | 239–241 | 68.51 | 5.87 | 15.92 | C20H20N4O2 |
| 36 | 2,6-$F_2$Ph | H | 216–218 | 62.36 | 3.75 | 12.01 | C18H13F2N3O2[g] |
| 37 | $c$-$C_6H_{11}$ | 7-OMe | 189–191 | 66.79 | 6.71 | 12.21 | C19H23N3O3 |
| 38 | $C_4H_9$ | H | 164–165 | 67.37 | 6.89 | 15.08 | C16H19N3O2 |

TABLE 6-continued

| CP # | R₁ | R | m p.° C. | C | H | N | Empirical Formula |
|---|---|---|---|---|---|---|---|
| 39 | 4-pyrimidinyl | H | 290–291 | 62.88 | 4.51 | 22.82 | C16H13N5O2 |
| 40 | 2-MeSPh | H | 188–190 | 64.78 | 4.54 | 11.95 | C19H17N3O2S |
| 41 | 6-quinolinyl | H | 279–283 (darkens) | 70.06 | 4.38 | 15.84 | C21H16N4O2[h] |
| 42 | 1,2,4-triazol-4-yl | H | 269–271 | 51.77 | 4.53 | 25.99 | C14H12N6O2[i] |
| 43 | c-C3H5 | H | 215–217 | 66.74 | 5.31 | 15.66 | C15H15N3O2 |
| 44 | 4-BrPh | H | 253–254 | 56.24 | 3.38 | 10.89 | C1BH14BrN3O2 |
| 45 | 4-FPh | H | 268–270 | 66.58 | 3.83 | 13.20 | C18H14FN3O2 |
| 46 | 2-pyrimidinyl | H | 236–238 (dec) | 59.85 | 4.28 | 21.72 | C16H13N5O2[j] |
| 47 | 2-NH2Ph | H | 212–213 | 67.71 | 5.15 | 17.51 | C18H16N4O2 |
| 48 | 6-indazolyl | H | 336–338 (bubbles) | 65.57 | 4.51 | 20.15 | C19H15N5O2 |
| 49 | 3-(1,2,4-triazinyl) | H | >320 | 58.18 | 3.77 | 27.46 | C15H12N6O2 |
| 50 | 5-indazolyl | H | 298–301 | 65.05 | 4.96 | 19.14 | C19H15N5O[k] |
| 51 | 7-benzofuranyl | H | 268–270 | 69.36 | 4.23 | 11.95 | C20H15N3O3 |
| 52 | 4-(2-Cl-pyridyl) | H | 290–292 | 59.67 | 3.76 | 16.44 | C17H13CIN4O2 |
| 53 | 2-(1,3,5-triazinyl) | H | 267–268 | 58.41 | 4.13 | 26.98 | C15H12N6O2 |
| 54 | 4-CNPh | H | 309–310 | 68.74 | 3.68 | 16.98 | C19H14N4O2 |
| 55 | 4-(tetraF-pyridyl) | H | 251–252 | 53.98 | 2.45 | 14.80 | C17H10F4N4O2 |
| 56 | 4-(N-Me-pyridyl) | H | 280–282 | 47.54 | 3.63 | 12.03 | C18H17N4O2.1[f] |
| 57 | 4-pyridyl | 7-OMe | 270–272 | 64.28 | 4.89 | 16.61 | C18H16N4O3 |
| 58 | 4-piperidinyl | H | 300–302 | 52.05 | 5.53 | 14.31 | C17H20N4O2.HBr |
| 59 | CH2(4-pyridyl) | H | 260–262 | 67.37 | 4.89 | 17.49 | C18H16N4O2 |
| 60 | 4-morpholinyl | H | 228–229 | 60.78 | 5.91 | 17.02 | C16H18N4O3[l] |
| 61 | 4-NH2SO2Ph | H | 304–306 | 56.62 | 4.26 | 14.52 | C18H16N4O4S |
| 62 | CH2(3-pyridyl) | H | 227–229 | 67.64 | 5.07 | 17.64 | C18H16N4O2 |
| 63 | 2-pyrazinyl | H | 297–300 | 62.36 | 4.30 | 22.96 | C16H13N5O2 |
| 64 | 5-Me-1,3,4-thiadiazol-2-yl | H | 296–298 | 54.43 | 3.80 | 21.02 | C15H13N5O2S |
| 65 | 5-isoquinolinyl | H | 293–295 | 70.59 | 4.41 | 15.75 | C21H16N4O2 |
| 66 | 4-(3-MeS-pyridyl) | H | 257–259 | 61.33 | 4.58 | 15.66 | C18H16N4O2S |
| 67 | 4-(3,5-Cl2-2,6-F2pyridyl) | H | 220–221 | 49.73 | 2.47 | 13.06 | C17H10Cl2F2N4O2 |
| 68 | 5-(3-Me-isoxazolyl) | H | 272–275 | 61.70 | 4.53 | 18.03 | C16H14N4O3 |
| 69 | 2-thiadiazolyl | H | 274–276 | 52.80 | 3.40 | 22.06 | C14H11N5O2S[m] |
| 70 | 3-(2-Cl-pyridyl) | H | 262–265 | 59.11 | 3.68 | 16.22 | C17H13CIN4O2[n] |
| 71 | 4-Et2NPh | H | 178–180 | 70.11 | 6.48 | 14.47 | C22H24N4O2 |
| 72 | 6-benzothiazolyl | H | 315–316 | 62.83 | 3.85 | 15.63 | C19H14N4O2S |
| 73 | 5-benzotriazolyl | H | 302–304 | 59.51 | 4.07 | 23.68 | C18H14N6O2[o] |
| 74 | 5-CF3-thiadiazolyl | H | 313–316 | 47.34 | 2.61 | 18.24 | C15H10F3N5O2S |
| 75 | 4-(3-Cl-pyridyl) | H | 257–259 | 59.86 | 3.91 | 16.43 | C17H13CIN4O2 |
| 76 | 4-quinaldinyl | H | 266–268 | 67.55 | 5.45 | 14.01 | C22H18N4O2[p] |
| 77 | 4-(3-Me-pyridyl) | H | 269–272 | 67.47 | 4.98 | 17.75 | C18H16N4O2 |
| 78 | 2-(3,5-(CF3)2pyridyl) | H | 240–241 | 51.58 | 2.41 | 12.93 | C19H12F6N4O2 |
| 79 | 2-MeS-4-Me2N-Ph | H | 170–172 | 63.73 | 5.38 | 14.32 | C21H22N4O2S |
| 80 | 4-Me2NPh | 7-Cl | 240–241 | 62.46 | 4.84 | 14.30 | C20H19CIN4O2 |
| 81 | Ph | 7-Cl | 270–273 | 63.55 | 4.08 | 12.21 | C18H14CIN3O2 |
| 82 | 4-pyridyl | 7-Cl | 289–292 | 59.77 | 3.68 | 16.34 | C17H13CIN4O2 |
| 83 | c-C4H7 | H | 217–219 | 67.17 | 6.10 | 14.72 | C16H17N3O2O[p] |
| 84 | Ph | 8-Cl | 267–269 | 63.63 | 3.99 | 12.61 | C18H14CIN3O2 |
| 85 | 2-Me-4-Me2NPh | H | 210–211 | 69.69 | 6.19 | 15.39 | C21H22N4O2 |
| 86 | 2-F-4-Me2NPh | H | 232–234 | 65.63 | 5.19 | 15.33 | C20H19FN4O2 |
| 87 | 2-Me2NPh | H | 217–218 | 68.88 | 5.76 | 16.19 | C20H20N4O2 |
| 88 | 4-pyridyl | 6-Me | 238–239 | 67.25 | 4.92 | 17.42 | C18H16N4O2 |
| 89 | Ph | 6-Me | 224–226 | 71.18 | 5.24 | 13.18 | C19H17N3O2 |
| 90 | 4-NH2COPh | H | 315–317 | 65.53 | 4.50 | 16.31 | C19H16N4O3 |
| 91 | C6F5 | H | 227–229 | 54.71 | 2.47 | 10.78 | C18H10F5N3O2 |
| 92 | 2,4-F2Ph | H | 202–204 | 63.35 | 3.65 | 12.49 | C18H13F2N3O2 |
| 93 | 2,4,6-F3Ph | H | 273–275 | 60.13 | 3.28 | 11.70 | C18H12F3N3O2 |
| 94 | 2-FPh | 6-Me | 269–272 | 67.72 | 4.79 | 12.57 | C19H16FN3O2 |
| 95 | 3-FPh | H | 266–268 | 66.71 | 4.29 | 13.18 | C18H14FN3O2 |
| 96 | 2,3,4-F3Ph | H | 299–302 | 59.90 | 3.27 | 11.73 | C18H12F3N3O2 |
| 97 | 4-(3F-pyridyl) | H | 283–285 | 62.85 | 4.11 | 17.10 | C17H13FN4O2 |
| 98 | 2,5-F2Ph | H | 290–292 | 63.01 | 3.82 | 12.25 | C18H13F2N3O2 |
| 99 | 2-imidazol | H | >380 | 60.09 | 4.24 | 23.16 | C15H13N5O2 |
| 100 | 4-(2-M-pyridyl) | H | 263–265 | 66.72 | 4.94 | 17.40 | C18H16N4O2 |
| 101 | 2,4,6-Cl3Ph | H | 240–242 | 52.71 | 2.71 | 10.08 | C18H12Cl3N3O2 |
| 102 | Me | H | 284–287 | 62.66 | 5.08 | 16.63 | C13H13N3O2[e] |
| 103 | 2-Br-4,6-F2Ph | H | 250–252 | 50.73 | 2.69 | 9.81 | C18H12BrF2N3O2 |
| 104 | 2,4,6-F3Ph | 7-Cl | 187–189 | 53.37 | 2.65 | 10.20 | C18H11CIF2N3O2 |
| 105 | 2-PrH | 194–196 | 66.16 | 6.39 | 15.46 | | C15H17N3O2 |

TABLE 6-continued

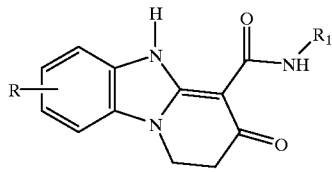

| CP # | R₁ | R | m p.° C. | C | H | N | Empirical Formula |
|---|---|---|---|---|---|---|---|
| 106 | 4-pyridyl | 7-F | 292–293 | 62.93 | 3.98 | 17.18 | C17H13FN4O2 |
| 107 | 2,4,6-F₃Ph | 7-F | 205–207 | 55.46 | 3.01 | 10.60 | C18H11F4N3O2<sup>q</sup> |
| 108 | 2-FPh | 7-F | 266–268 | 62.15 | 3.77 | 11.99 | C18H13F2N3O2<sup>e</sup> |
| 109 | 2,6-F₂Ph | 7-F | 214–216 | 59.79 | 3.14 | 11.62 | C18H12F3N3O2 |
| 110 | 4-(3-F-pyridyl) | 7-F | 284–287 | 58.22 | 3.33 | 15.80 | C17H12F2N4O2<sup>f</sup> |
| 111 | 2,4-F₂Ph | 7-F | 274–276 | 59.90 | 3.04 | 11.57 | C18H12F3N3O2 |
| 112 | 2,6-Cl₂Ph | 7-F | 164–166 | 54.42 | 2.72 | 10.41 | C18H12C12FN3O2<sup>e</sup> |
| 113 | 2-FPh | 7-Cl | 265–267 | 60.47 | 3.18 | 11.79 | C18H13ClFN3O2 |
| 114 | 2,6-F₂Ph | 7-Cl | 212–213 | 56.55 | 3.14 | 11.06 | C18H12ClF2N3O2<sup>s</sup> |
| 115 | 4-(2-Me₂NCH₂CH₂)Ph | H | 239–241 | 62.92 | 6.15 | 13.14 | C22H24N4O2.HCl<sup>a</sup> |
| 116 | 3-(2-F-pyridyl) | H | 284–286 | 62.87 | 3.82 | 17.01 | C17H13FN4O2 |

Solvates present (moles): <sup>a</sup>0.60 H2O; <sup>b</sup>0.25 THF; <sup>c</sup>0.60 acetone; <sup>d</sup>0.37 H2O; <sup>e</sup>0.25 H2O; <sup>f</sup>0.10 CH2Cl2; <sup>g</sup>0.05 CH2Cl2; <sup>h</sup>0.12 CH3OH; <sup>i</sup>1.50 H2O; <sup>j</sup>0.62 H2O; <sup>k</sup>0.33 CH3OH.0.25 H2O; <sup>l</sup>0.16 2-propanol; <sup>m</sup> 0.10 H2O; <sup>n</sup>0.15 H2O; <sup>o</sup>0.80 H2O; <sup>p</sup>1.0 H2O; <sup>q</sup>0.20 CH2Cl2; <sup>r</sup>0.20 CH3OH.0.20 H2O; <sup>s</sup>0.40 H2O.

EXAMPLE 3

Phenyl-1,2-dihydro-3-hydroxypyrido(1,2-a) benzimidazole-4-carboxthiolate (CP #119)

A mixture of the pyridobenzimidazo derivative VII (5.16 g, 0.02 M) prepared as in Example 1 and thiophenol (11.0 g, 0.10 M) in xylenes (200 mL) was heated to reflux under argon for 4.5 h. An additional portion of thiophenol was added (11.0 g, 0.10 M) and the reaction mixture was heated at reflux for another 8 h followed by stirring at room temperature for 16 h. Yet another portion of thiophenol was added to the reaction mixture (11.0 g, 0.10 M) followed by an additional 6 h of heating at reflux. The resulting yellow solid precipitate was isolated, washed with xylenes and left to air dry. This solid was purified by HPLC, using methylene chloride and THF as eluents followed by recrystallization of the desired fractions from methylene chloride and acetone to give the title compound as a solid: mp 220–222° C.; MS: 323 (MH⁺).

Anal. Calcd for $C_{18}H_{14}N_2O_2S$: C, 67.06; H, 4.38; N, 8.69. Found: C, 67.17; H, 4.29; N, 8.43.

EXAMPLE 4

Phenyl-1,2-dihydro-3-hydroxypyrido(1,2-a) benzimidazole-4-carboxylate (CP #118)

A mixture of the pyridobenzimidazo derivative VII prepared as in Example 1 (3.5 g, 13.6 mM) and phenol (7.0 g, 74.5 mM) in xylenes (350 mL) was heated to reflux under argon for 6 h and left at room temperature for 16 h. The resulting solid precipitate was filtered and the filtrate was concentrated in vacuo. The resulting residue was purified by HPLC, using methylene chloride and THF as eluents followed by recrystallization of the desired fractions from methylene chloride and acetone to give the title compound as a solid: mp 176–178° C.; MS: 307 (MH⁺).

Anal. Calcd for $C_{18}H_{14}N_2O_3 \cdot 0.25\ CH_2Cl_2$: C, 66.92; H, 4.46; N, 8.55. Found: C, 67.62; H, 4.26; N, 8.59.

EXAMPLE 5

1,2-Dihydro-5-ethyl-3-oxo-N-(2-fluorophenyl)-pyrido(1,2-a)benzimidazole-4-carboxamide (CP #123)

50% Sodium hydride in oil (Et₂O washed: 2.4 g, 50 mmol) was added (portionwise) to a suspension of the pyridobenzimidazo derivative VII (13.0 g, 50 mmol) prepared as in Example 1 and DMF (150 mL) at 5–10° C. under argon. The reaction mixture was stirred for 15 min at 10° C. and an additional portion of DMF (50 mL) was added. A solution of ethyl iodide (4.4 mL, 55 mmol) in DMF (10 mL) was added portionwise to the reaction mixture at 10° C. and upon completion of the addition said mixture was allowed to warm to room temperature and stirred overnight. An additional portion of sodium hydride (1.2 g, 25 mmol) and ethyl iodide (4.3 g, 25 mmol) was added to the reaction mixture at room temperature and the mixture was stirred at that temperature for 24 h. The resulting mixture was poured into dilute NaOH(aq) and extracted with several portions of methylene chloride. The combined organic extracts were washed with NaOH(aq) and water, dried with K₂CO₃ and concentrated in vacuo to give alkylated pyridobenzimidazo derivative XI (R=H, R₂=Et) as an oil which was used without further purification. ¹H NMR (CDCl₃, 300 MHz): δ7.4–7.2 (m, 4H), 4.35 (broad s, 2H), 4.16 (m, 4H), 2.74 (dd, 2H), 1.40 (t, 6H).

3N Sodium hydroxide solution (50 mL, 150 mM) was added to a solution of the alkylated pyridobenzimidazo derivative XI (R=H, R₂=Et: 5.0 g, 17.4 mM) in EtOH (125 mL) and heated to reflux for 2 h. An additional portion of sodium hydroxide (20 mL) solution was added to the reaction mixture and the resulting mixture was heated to reflux for 4 h and stirred at room temperature overnight. Yet another portion of sodium hydroxide solution (10 mL) was added to the mixture followed by heating said mixture to reflux for 2 h. The resulting mixture was concentrated in vacuo and partitioned between water and chloroform. The aqueous layer was washed with several portions of chloroform and the combined organic extracts were dried (K₂CO₃) and concentrated in vacuo to give the decarboxylated pyridobenzimidazo derivative XII (R=H, R₂=Et) as a solid which was used without further purification. ¹H NMR (CDCl₃, 300 MHz): d 7.20–7.0 (m,4H), 4.96 (s, 1 H), 4.09 (dd, 2H), 3.88 (q, 2H), 2.74 (dd, 2H), 1.35 (t, 3H).

2-Fluorophenyl isocyanate (2.32 g, 17.0 mM) was added to a stirred solution of the decarboxylated pyridobenzimidazo derivative XII (R=H, R₂=Et: 2.90 g, 13.5 mM) at room temperature under argon. The mixture was stirred for 2 h and concentrated in vacuo. The residue was treated with EtOH and Et₂O and the resulting powdery solid was isolated and recrystallized from methylene chloride and EtOH to give the title compound as a solid: mp 141.5–143° C.; MS: 351 (MH⁺).

Anal. Calcd for $C_{20}H_{18}FN_3O_2$: C, 68.36; H, 5.16; N, 11.96. Found: C, 68.37; H, 5.14; N, 11.96.

EXAMPLE 6

The following general procedure was used in the synthesis of the compounds listed in Table 7:

50% Sodium hydride in oil (Et₂O washed: 1 molar equivalent) was added (portionwise) to a suspension of the an appropriately substituted pyridobenzimidazo derivative VII (1 molar equivalent) in a suitable solvent at 5–10° C. under argon. The reaction mixture was stirred for 15 min at 10° C. A solution of an appropriate alkylating agent (1.1 molar equivalents) in a suitable solvent was added portionwise to the reaction mixture at 10° C. and the resulting mixture was allowed to warm to room temperature and stirred overnight. Additional portions of sodium hydride and the alkylating agent can be added if needed to force the reaction to completion. The resulting mixture was poured into dilute NaOH(aq) and extracted with several portions of an organic solvent. The combined organic extracts were washed with NaOH(aq) and water, dried with K₂CO₃ and concentrated in vacuo to give alkylated pyridobenzimidazo derivative XI, which was used without further purification.

An aqueous sodium hydroxide solution (10 molar equivalents) was added to a solution of the alkylated pyridobenzimidazo derivative XI (1 molar equivalent) in a suitable solvent and heated to reflux for 2–16 h. Additional portions of sodium hydroxide solution may be added to the reaction mixture followed by continued heating in order to force the reaction to completion. The resulting mixture was concentrated in vacuo and partitioned between water and an organic solvent. The aqueous layer was washed with several portions of the selected solvent and the combined organic extracts were dried (K₂CO₃) and concentrated in vacuo to give the decarboxylated alkylated pyridobenzimidazo derivative XII, which was used without further purification.

A suitable isocyanate (1.25 molar equivalents) was added to a stirred solution of the decarboxylated pyridobenzimidazo derivative XII (1 molar equivalent) in a suitable solvent at room temperature under argon. The mixture was stirred for 2 h and concentrated in vacuo. The residue was treated with EtOH and Et₂O and the resulting solid was isolated and recrystallized from a suitable solvent to give the desired carboxamide XIII as a solid.

TABLE 7

| CP # | R1 | R2 | R4 | mp. ° C. | C | H | N | Empirical Formula |
|---|---|---|---|---|---|---|---|---|
| 120 | Ph | Me | H | 205–206 | 70.84 | 5.66 | 12.98 | C19H17N3O2 |
| 121 | Ph | Et | H | 223.5–224.5 | 71.71 | 5.64 | 12.46 | C20H19N3O2 |
| 122 | 2-FPh | Me | H | 196–197 | 67.68 | 4.74 | 12.45 | C19H16FN3O2 |
| 124 | 4-Me₂NPh | Me | H | 177–179 | 69.27 | 6.05 | 15.80 | C21H22N4O2 |
| 125 | 4-Me₂NPh | Et | H | 213–214 | 69.94 | 6.37 | 14.94 | C22H24N4O2 |
| 126 | 4-pyridyl | Me | H | 242–243 | 67.17 | 4.94 | 17.49 | C18H16N4O2 |
| 127 | Ph | CH₂Ph | H | 216–218 | 75.95 | 5.31 | 10.53 | C25H21N3O2 |
| 128 | 2-FPh | CH₂Ph | H | 245–247 | 71.98 | 4.90 | 10.39 | C25H20FN3O2 |
| 129 | 2,4-F₂Ph | CH₂Ph | H | 223–226 | 69.57 | 4.36 | 9.65 | C25H19F2N3O2 |
| 130 | 2-FPh | Pr | H | 193–195 | 67.53 | 5.43 | 11.13 | C21H20FN3O2 |
| 131 | 2,4-F₂Ph | Pr | H | 197–199 | 65.29 | 4.92 | 10.77 | C21H19F2N3O2 |
| 132 | 2-F-Ph | Me | Me | 175–177 | 67.70 | 5.23 | 11.82 | C20H18FN3O2 |
| 133 | 4-pyridyl | Et | H | 192–194 | 67.94 | 5.48 | 16.60 | C19H18N4O2 |
| 134 | Ph | Me | Me | 170-172 | 71.90 | 5.70 | 12.49 | C20H19N3O2 |
| 135 | 2,4,6-F₃Ph | Me | H | 231–233 | 60.69 | 3.69 | 11.13 | C19H14F3N3O2 |
| 136 | Ph | Pr | H | 158–161 | 72.44 | 6.02 | 12.11 | C21H21N3O2 |
| 137 | 2,4,6-F₃Ph | Pr | H | 204–206 | 62.64 | 4.46 | 10.22 | C21H18F3N3O2 |

EXAMPLE 7

N-(2,6-Difluorophenyl)-3-hydroxypyrido(1,2-a) benzimidazole-4-carboxamide (CP #141)

A mixture of the substituted pyridobenzimidazo derivative VIII (R=H, R₁=2,6-difluorophenyl: 5.20 g, 15.2 mmol) and activated MnO₂ (10.0 g, 120 mmol) in xylene (100 mL) was heated to reflux for 5 h, stirred at room temperature overnight and heated once again at reflux for 24 h. An additional portion of MnO₂ (10.0 g, 120 mmol) was added to the brew followed by another 5 h of heating at reflux. The mixture was cooled to room temperature, diluted with chloroform/MeOH 3:1 and filtered to remove the solid manganese oxides. The filter cake was washed with several portions of the solvent mixture and the combined filtrates were dried (K₂CO₃) and concentrated in vacuo. The residue was purified by HPLC (EtOAc eluent) and recrystallization from methylene chloride and EtOH to give the title compound as a solid: mp 232–235° C.; MS: 340 (MH⁺).

Anal. Calcd for $C_{18}H_{11}F_2N_3O_2$.0.17 EtOH: C, 63.46; H, 3.49; N, 12.11. Found: C, 63.36; H, 3.70; N, 11.67.

EXAMPLE 8

The following procedure was used in the synthesis of the compounds listed in Table 8.

A mixture of an appropriately substituted pyridobenzimidazo derivative VIII or XIII (1 molar equivalent) and activated MnO₂ (8 molar equivalents) in a suitable solvent was heated to reflux for 5 hours–2 days. An additional portion of MnO₂ may be added if needed to drive the reaction to completion. The mixture was cooled to room temperature, diluted with a suitable solvent and filtered to remove the solid manganese oxides. The filter cake was washed with several portions of the solvent mixture and the combined filtrates were dried (K₂CO₃) and concentrated in vacuo. The residue was purified using any combination of standard techniques which include chromatography and recrystallization to give the oxidized derivative XV as a solid.

TABLE 8

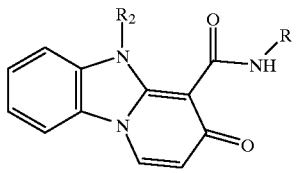

| CP # | R₁ | R₂ | mp. °C. | C | H | N | Empirical Formula |
|---|---|---|---|---|---|---|---|
| 138 | Ph | H | 264.0–266.0 | 71.13 | 4.32 | 13.76 | C18H13N3O2 |
| 140 | 4-pyridyl | H | 313–315 | 65.35 | 4.30 | 17.75 | C17H12N4O2.1/2 MeOH |
| 142 | Ph | Me | 219.5–220.5 | 71.81 | 4.36 | 13.31 | C19H15N3O2 |

EXAMPLE 9

N-(2-Fluorophenyl)-3-hydroxypyrido(1,2-a) benzimidazol-4-carboxamide 1¼ Hydrate (CP #139)

A mixture of a pyridobenzimidazo derivative VIII (R=H, R₁=2-FPh: 3.75 g, 11.6 mM) and 2,3-dichloro-5,6-dicyano-1,4-benzoquinone (DDQ: 4.54 g, 20.0 mM) in 1,4-dioxane (150 ml) was heated to reflux for 8 h and stirred at room temperature overnight. An additional portion of DDQ (2.0 g, 8.8 mM) was added and the mixture was heated at reflux for 4 h and concentrated in vacuo. The residue was purified by HPLC using EtOAc as an eluent and recrystallization from methylene chloride and MeOH gave the title compound as a solid: mp 237–238° C.; MS: 322 (MH⁺).

Anal. Calcd for C₁₈H₁₂FN₃O₂.¼H₂O: C, 66.36; H, 3.87; N, 12.90. Found: C, 66.51; H, 4.06; N, 13.01.

EXAMPLE 10

1,2-Dihydro-3-hydroxy-N-phenylpyrido(1,2-a) benzimidazole-4-thiocarboxamide (CP #117)

A mixture of the substituted pyridobenzimidazo derivative VIII (R₁=Ph: 4.50 g, 14.75 mM) and Lawesson's reagent (2,4-bis(4-methoxyphenyl)-1,3-dithia-2,4-diphosphetane-2,4-disulfide; 3.57 g, 8.85 mM) in anhydrous toluene (30 mL) was placed in an oilbath at 85° C. under argon. The mixture was heated to 95° C. and kept at that temperature for 2.75 h and cooled to room temperature. The resulting yellow precipitate was isolated, washed with EtOH and recrystallized from a mixture of methylene chloride and EtOH to give the title compound as a white solid: mp 224–227° C.; MS: 322 (MH⁺).

Anal. Calcd for C₁₈H₁₅N₃OS: C, 67.27; H, 4.70; N, 13.07. Found: C, 67.13; H, 4.62; N, 13.02.

EXAMPLE 11

N-(2-Fluorophenyl)-6-methyl-4-oxo-1,2,3,4-tetrahydro-6H-azepino(1,2-a)benzimidazol-5-carboxamide (CP #147)

2-Fluorophenylisocyanate (0.28 g, 2.06 mmol) was added to a solution of 6-methyl-1,2,3,4-tetrahydro-4-oxo-6H-azepino(1,2-a)benzimidazole (0.4 g, 1.87 mmol; Ohta, S. et al. *Chem. Pharm. Bull.* 1990, 38(2), 301) in methylene chloride (5 mL) and the reaction mixture was stirred at room temperature for 16 h. The reaction was concentrated in vacuo and purified by medium pressure chromatography, using EtOAc/MeOH as an eluent and recrystallization from EtOAc/methylene chloride to give the title compound as a solid: mp 139–141° C.; MS: 352 (MH⁺).

Anal. Calcd for C₂₀H₁₈FN₃O₂.½EtOAc: C, 66.82; H, 5.61; N, 10.63. Found: C, 66.88; H, 5.58; N, 10.73.

EXAMPLE 12

The following general procedure was used in the synthesis of compounds listed in Table 9. The 6-benzyl substituted starting material was prepared following the method of Ohta, S. et al. *Chem. Pharm. Bull.* 1990, 38(2), 301.

The 6-substituted -1,2,3,4-tetrahydro-4-oxo-6H-azepino (1,2-a) benzimidazole (ca. 2 mmol) in methylene chloride (5 mL) was stirred at room temperature as the appropriate isocyanate (2.2 mmol) was added in slowly. When the reaction was complete, the solvent was evaporated and the residue was purified by preparative hplc or by recrystallization from an appropriate solvent to give the desired derivative XXI.

TABLE 9

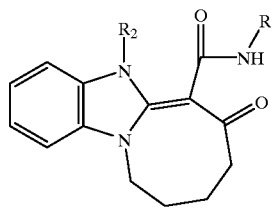

| CP # | R₁ | R₂ | mp. °C. | C | H | N | Empirical Formula |
|------|-----|-----|---------|-------|------|-------|-------------------|
| 144 | Ph | Me | 118–120 | 70.04 | 6.18 | 11.05 | C20H19N3O2.0.5C4H8O2 |
| 150 | 4-Me₂NPh | Me | 248–250 | 70.23 | 6.48 | 14.94 | C22H24N4O2 |
| 153 | 4-pyridyl | Me | 255–257 | 68.07 | 5.23 | 16.64 | C19H18N4O2 |
| 145 | Ph | Bzl | 219–220 | 76.00 | 5.61 | 10.11 | C26H23N3O2 |
| 148 | 2-FPh | Bzl | 246–248 | 72.43 | 5.05 | 9.69 | C26H22FN3O2 |
| 156 | 2,4-F₂Ph | Bzl | 228–229 | 69.89 | 4.69 | 9.36 | C26H21F2N3O2 |
| 154 | 4-pyridyl | Bzl | 144–147 | 70.88 | 5.38 | 13.08 | C25H22N4O2.0.75H2O |
| 151 | 4-Me₂NPh | Bzl | 221–224 | 73.60 | 6.19 | 12.08 | C28H28N4O2.0.2H2O |
| 157 | 2,4,6-F₃Ph | Me | 235–237 | 61.76 | 4.06 | 10.68 | C20H16F3N3O2 |

EXAMPLE 13

N-(2,4-Difluorophenyl)-4-oxo-1,2,3,4-tetrahydro-6H-azepino(1,2-a)benzimidazol-5-carboxamide (CP #155)

20% Palladium hydroxide/carbon (2–5 g, 3.5 mmol) was added to a solution of the amido derivative XXI (R₂=benzyl, R₁=2,4-difluorophenyl: 0.78 g, 2.0 mmol) in EtOH (200 mL) and this mixture was placed in a Parr apparatus and pressurized with hydrogen at 50 psi for 24 h. An additional portion of palladium hydroxide/C (0.5 g) was added to the reaction mixture followed by another 4 h of shaking under hydrogen at 50 psi. The resulting mixture was filtered and concentrated in vacuo. The residue was recrystallized from EtOAc to give the title compound as a solid: mp 221–222° C.

Anal. Calcd for $C_{19}H_{15}F_2N_3O_2 \cdot H_2O$: C, 61.12; H, 4.59; N, 11.25. Found: C, 60.78; H, 4.23; N, 11.01.

EXAMPLE 14

The following general procedure was used in the synthesis of the compounds listed in Table 10.

20% Palladium hydroxide on carbon (ca. 2 molar equivalents) was added to a solution of an appropriately substituted amido derivative XXI (R₂=benzyl; 1.0 molar equivalent) in EtOH and this mixture was placed in a Parr apparatus and pressurized with hydrogen at 50 psi until all the starting material was consumed. The resulting mixture was filtered and concentrated in vacuo and recrystallized from an appropriate solvent to give the desired derivative XXII.

TABLE 10

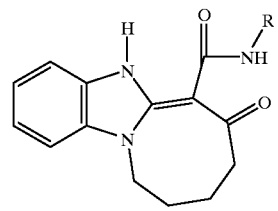

| CP # | R₁ | mp. °C. | C | H | N | Empirical Formula |
|------|-----|---------|-------|------|-------|-------------------|
| 143 | Ph | 163–166 | 70.20 | 5.22 | 12.72 | C19H17N3O2.0.2H2O |
| 146 | 2-FPh | 196–197 | 65.70 | 4.61 | 11.83 | C19H16FN3O2.0.5H2O |
| 149 | 4-Me₂NPh | 148–151 | 68.95 | 6.36 | 14.63 | C21H22N4O2.0.1H2O |
| 152 | 4-pyridyl | 197–201 | 66.33 | 5.77 | 15.63 | C18H16N4O2.0.25H2O |

What is claimed is:

1. A compound of the following formula I:

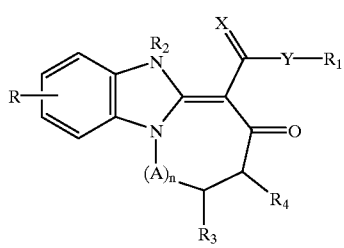

I wherein
- R₁ is selected from the group consisting of cycloalkyl (C₃–C₁₀), aralkyl, substituted aralkyl, a heterocycle, a substituted heterocycle, piperidin-3-yl, piperidin-2-yl, morpholin-4-yl, heterocyclic-CH₂—, heterocyclic-CH₂CH₂—, substituted heterocyclic-CH₂— and heterocyclic-CH₂CH₂—; wherein the heterocycle is selected from the group consisting of pyridinyl, thiazolyl, thiophenyl, furanyl, indolyl, benzothiophenyl, pyridazinyl, pyrimidinyl, indolyl, indolinyl, quinolinyl, indazolyl, imidazolyl, benzofuranyl, triazinyl, pyrazinyl, isoquinolinyl, isoxazolyl, thiadiazolyl, benzothiazolyl, triazolyl and benzotriazolyl;
- R₂ is selected from any of hydrogen, alkyl(C₁–C₁₂), cycloalkyl(C₃–C₁₀), aralkyl and substituted aralkyl;
- R is independently selected from one or more of the group consisting of hydrogen, alkyl (C₁–C₈), halogen, perfluoro(lower)alkyl, hydroxy, lower alkoxy, di(lower alkyl)amino, lower alkoxycarbonyl and (lower alkyl)thio;
- n is 1;
- A is selected from methylene or substituted methine where the substituents are selected from the group consisting of alkyl (C₁–C₂);
- R₃ and R₄ are independently selected from the group consisting of hydrogen and alkyl (C₁₋₃) or are taken together to form a double bond;
- X is selected from the group consisting of oxygen and sulfur;
- Y is selected from the group consisting of NH, oxygen and sulfur, provided that when R₁ is an alkyl or a heterocycle, Y may not be sulfur or oxygen;
- Y and R₁ may also be taken together to form an NH₂ group;
- in the case of substituted aralkyl, there are one or more substituents which are independently selected from the group consisting of halogen, alkyl (C₁–C₅), perfluoro(lower)alkyl, nitro, lower alkoxy, hydroxy, amino, lower alkylamino, di(lower alkyl)amino, di(lower alkyl)aminoalkyl, carboxy, lower alkoxycarbonyl, carboxamide, lower alkylthio, cyano, and aminosulfonyl;
- in the case of substituted heterocycle and substituted heterocyclic —CH₂— and heterocyclic —CH₂CH₂—, there are one or more substituents, which are independently selected from the group consisting of halogen, perfluoro(lower)alkyl, nitro, lower alkylthio, lower alkoxy, lower alkyl, di(lower alkyl)amino, carboxy, and lower alkoxycarbonyl;
- or a pharmaceutically acceptable salt, solvate, hydrate, tautomer or rotomer thereof.

2. The compound of claim 1, wherein R₁ is selected from the group consisting of alkyl (C₁–C₁₂), cycloalkyl (C₃–C₁₀), phenyl, substituted phenyl, aralkyl, pyridinylmethyl, a heterocycle or substituted heterocycle selected from any of pyridinyl, thiazolyl, pyrimidinyl, indolinyl, quinolinyl, indazolyl, benzofuranyl, triazinyl, pyrazinyl, isoquinolinyl, isoxazolyl, thiazolyl, thiodiazolyl, benzothiazolyl, triazolyl, or benzotriazolyl.

3. The compound of claim 2, wherein the substituted heterocycles are selected from the group consisting of substituted pyridinyl, substituted isoxazolyl, substituted thiadiazolyl, and substituted quinolinyl.

4. The compound of claim 1, wherein R₂ is selected from any of H, lower alkyl or aralkyl.

5. The compounds of claim 1, wherein there is one R substitutent.

6. The compound of claim 5, wherein R is selected from the group consisting of lower alkoxy, halogen, perfluorolower alkyl, and alkyl (C₁–C₁₂).

7. The compound of claim 1, wherein R₃ and R₄ are either hydrogen or are taken together to form a double bond.

8. The compound of claim 1, wherein X is oxygen and Y is NH.

9. The compound of claim 1, wherein X is S and Y is NH.

10. The compound of claim 1, wherein X is oxygen and Y is S or O.

11. The compound of claim 1 selected from the group consisting of:
6-benzyl-N-(4-pyridyl)-4-oxo-1,2,3,4-tetrahydro-6H-azepino(1,2-a)benzimidazole-5-carboxamide,
6-methyl-4-oxo-N-(4-pyridyl)-1,2,3,4-tetrahydro-6H-azepino(1,2-a)benzimidazole-5-carboxamide, and
4-oxo-N-(4-pyridyl-1,2,3,4-tetrahydro-6H-azepino(1,2-a)benzimidazole-5-carboxamide.

12. A pharmaceutical composition comprising a compound of formula I:

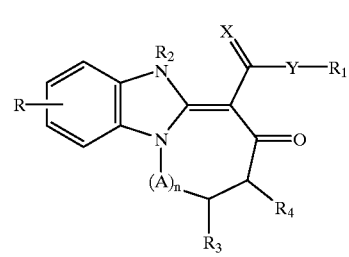

wherein
- R₁ is selected from the group consisting of cycloalkyl (C₃–C₁₀), aralkyl, substituted aralkyl, a heterocycle, a substituted heterocycle, piperidin-3-yl, piperidin-2-yl, morpholin-4-yl, heterocyclic-CH₂—, heterocyclic-CH₂CH₂—, substituted heterocyclic-CH₂— and heterocyclic-CH₂CH₂—; wherein the heterocycle is selected from the group consisting of pyridinyl, thiazolyl, thiophenyl, furanyl, indolyl, benzothiophenyl, pyridazinyl, pyrimidinyl, indolyl, indolinyl, quinolinyl, indazolyl, imidazolyl, benzofuranyl, triazinyl, pyrazinyl, isoquinolinyl, isoxazolyl, thiadiazolyl, benzothiazolyl, triazolyl and benzotriazolyl;
- R₂ is selected from any of hydrogen, alkyl(C₁–C₁₂), cycloalkyl (C₃–C₁₀ aralkyl and substituted aralkyl;
- R is independently selected from one or more of the group consisting of hydrogen, alkyl (C₁–C₈), halogen, perfluoro(lower)alkyl, hydroxy, lower alkoxy, di(lower alkyl)amino, lower alkoxycarbonyl and (lower alkyl)thio;
- n is 1;
- A is selected from methylene or substituted methine where the substituents are selected from the group consisting of alkyl (C₁–C₂);
- R₃ and R₄ are independently selected from the group consisting of hydrogen and alkyl (C₁₋₃) or are taken together to form a double bond;
- X is selected from the group consisting of oxygen and sulfur;
- Y is selected from the group consisting of NH, oxygen and sulfur, provided that when R₁ is an alkyl or a heterocycle, Y may not be sulfur or oxygen;

Y and $R_1$ may also be taken together to form an $NH_2$ group;

in the case of substituted aralkyl, there are one or more substituents which are independently selected from the group consisting of halogen, alkyl ($C_1$–$C_5$), perfluoro(lower)alkyl, nitro, lower alkoxy, hydroxy, amino, lower alkylamino, di(lower alkyl)amino, di(lower alkyl)aminoalkyl, carboxy, lower alkoxycarbonyl, carboxamide, lower alkylthio, cyano, and aminosulfonyl;

in the case of substituted heterocycle and substituted heterocyclic —$CH_2$— and heterocyclic —$CH_2CH_2$—, there are one or more substituents, which are independently selected from the group consisting of halogen, perfluoro(lower)alkyl, nitro, lower alkylthio, lower alkoxy, lower alkyl, di(lower alkyl)amino, carboxy, and lower alkoxycarbonyl;

or a pharmaceutically acceptable salt, solvate, hydrate, tautomer or rotomer thereof;

in an amount effective for treating disorders of the central nervous system and a pharmaceutically acceptable carrier or diluent.

13. A method for treating a disorder of the central nervous system selected from the group consisting of anxiety, muscle spasms, sleeplessness, convulsions and benzodiazepine overdoses comprising administering a compound of the formula I:

wherein $R_1$ is selected from the group consisting of cycloalkyl ($C_3$–$C_{10}$), aralkyl, substituted aralkyl, a heterocycle, a substituted heterocycle, piperidin-3-yl, piperidin-2-yl, morpholin-4-yl, heterocyclic-$CH_2$—, heterocyclic-$CH_2CH_2$—, substituted heterocyclic-$CH_2$— and heterocyclic-$CH_2CH_2$—; wherein the heterocycle is selected from the group consisting of pyridinyl, thiazolyl, thiophenyl, furanyl, indolyl, benzothiophenyl, pyridazinyl, pyrimidinyl, indolyl, indolinyl, quinolinyl, indazolyl, imidazolyl, benzofuranyl, triazinyl, pyrazinyl, isoquinolinyl, isoxazolyl, thiadiazolyl, benzothiazolyl, triazolyl and benzotriazolyl;

$R_2$ is selected from any of hydrogen, alkyl ($C_1$–$C_{12}$), cycloalkyl ($C_3$–$C_{10}$), aralkyl and substituted aralkyl;

R is independently selected from one or more of the group consisting of hydrogen, alkyl ($C_1$–$C_8$), halogen, perfluoro(lower)alkyl, hydroxy, lower alkoxy, di(lower alkyl)amino, lower alkoxycarbonyl and (lower alkyl)thio;

n is 1;

A is selected from methylene or substituted methine where the substituents are selected from the group consisting of alkyl ($C_1$–$C_2$);

$R_3$ and $R_4$ are independently selected from the group consisting of hydrogen and alkyl ($C_{1-3}$) or are taken together to form a double bond;

X is selected from the group consisting of oxygen and sulfur;

Y is selected from the group consisting of NH, oxygen and sulfur, provided that when $R_1$ is an alkyl or a heterocycle, Y may not be sulfur or oxygen;

Y and $R_1$ may also be taken together to form an $NH_2$ group;

in the case of substituted aralkyl, there are one or more substituents which are independently selected from the group consisting of halogen, alkyl ($C_1$–$C_5$), perfluoro(lower)alkyl, nitro, lower alkoxy, hydroxy, amino, lower alkylamino, di(lower alkyl)amino, di(lower alkyl)aminoalkyl, carboxy, lower alkoxycarbonyl, carboxamide, lower alkylthio, cyano, and aminosulfonyl;

in the case of substituted heterocycle and substituted heterocyclic —$CH_2$— and heterocyclic —$CH_2CH_2$—, there are one or more substituents, which are independently selected from the group consisting of halogen, perfluoro(lower)alkyl, nitro, lower alkylthio, lower alkoxy, lower alkyl, di(lower alkyl)amino, carboxy, and lower alkoxycarbonyl;

or a pharmaceutically acceptable salt, solvate, hydrate, tautomer or rotomer thereof;

to a mammal afflicted with a disorder of the central nervous system in an amount effective for treating such disorder.

14. The method of claim 13, wherein the effective amount is of from about 0.2 to 25 mg/kg per day.

15. The method of claim 13, wherein the disorder is anxiety.

16. The method of claim 13 wherein the disorder is convulsions.

17. The method of claim 13 wherein the disorder is sleeplessness.

18. The method of claim 13 wherein the disorder is muscle spasm.

19. The method of claim 13 wherein the disorder is benzodiazepine drug overdose.

* * * * *